United States Patent [19]

Smith

[11] Patent Number: 4,800,495
[45] Date of Patent: Jan. 24, 1989

[54] METHOD AND APPARATUS FOR PROCESSING SIGNALS USED IN OXIMETRY

[75] Inventor: Robert E. Smith, Edmonds, Wash.
[73] Assignee: Physio-Control Corporation, Redmond, Wash.
[21] Appl. No.: 897,750
[22] Filed: Aug. 18, 1986
[51] Int. Cl.$^4$ .............................................. G06F 15/42
[52] U.S. Cl. ..................... 364/413.03; 364/413.09; 356/41; 128/664
[58] Field of Search ................ 364/415, 416, 417; 128/637, 664, 663, 666; 356/41

[56] References Cited

U.S. PATENT DOCUMENTS

| | | | |
|---|---|---|---|
| 2,706,927 | 4/1955 | Wood | 88/14 |
| 3,647,299 | 3/1972 | Lavallee | 756/41 |
| 3,704,706 | 12/1972 | Herczfeld et al. | 128/2 L |
| 3,847,483 | 11/1974 | Shaw et al. | 128/2 L |
| 3,996,926 | 12/1976 | Birnbaum | 128/2.05 A |
| 3,998,550 | 12/1976 | Konishi et al. | 356/39 |
| 4,037,151 | 7/1977 | Takeuchi | 324/78 R |
| 4,086,915 | 5/1978 | Kofsky et al. | 128/2 L |
| 4,114,604 | 1/1978 | Shaw et al. | 356/41 |
| 4,140,110 | 2/1979 | Jansen | 128/2.05 A |
| 4,167,331 | 9/1979 | Nielsen | 356/39 |
| 4,201,222 | 5/1980 | Haase | 128/634 |
| 4,266,554 | 5/1981 | Hamaguri | 128/633 |
| 4,407,290 | 10/1983 | Wilber | 128/633 |
| 4,453,218 | 6/1984 | Sperinde | 364/416 |

FOREIGN PATENT DOCUMENTS 83304939.8 8/1983 European Pat. Off. .

Primary Examiner—Jerry Smith
Assistant Examiner—Steven G. Kibby
Attorney, Agent, or Firm—Christensen, O'Connor, Johnson & Kindness

[57] ABSTRACT

The present invention relates to the processing of signals containing information about the pulse rate and oxygen saturation of arterial blood flowing in tissue. These signals have a relatively periodic pulsatile component superimposed upon a varying baseline component. To determine the pulse rate and oxygen saturation from the signals, the positive peaks, negative peaks, and period of the signal must be determined. The present invention accomplishes this by first searching for a sustained positive sloping region of the signal. Then the first derivative of the signal with respect to time is analyzed and points on the signal before and after the occurrence of a slope reversal marked. If the slope at the first point is positive, the interval between the two points is searched for a maximum amplitude that is identified as a positive peak. After the occurrence of a negative sloping region of the signal, another pair of points are marked occurring before and after a subsequent slope reversal. The minimum amplitude of the signal between these points is then identified as a negative peak. For improved accuracy, these positive and negative peaks are then compared with waveform templates to determine whether the amplitude between the peaks falls within an allowable range and to determine whether the interval between the peaks likewise falls within an acceptable range. These ranges are adjustable in proportion to the amplitude and interval compared against them. In this manner, values for the positive peak, negative peak, and period of the signal can be determined with high reliability.

43 Claims, 16 Drawing Sheets

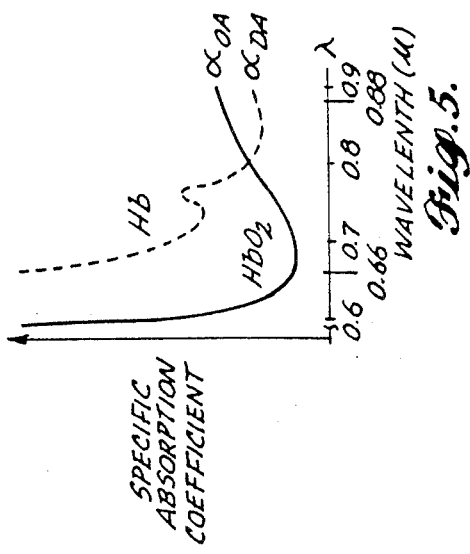
Fig. 4.
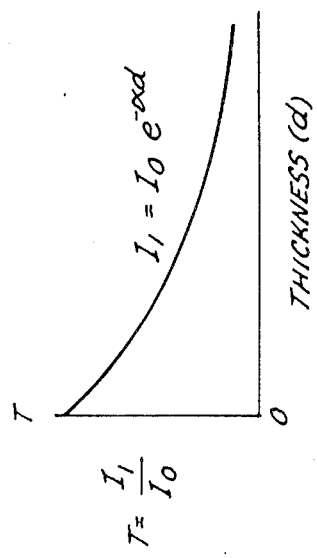
Fig. 5.
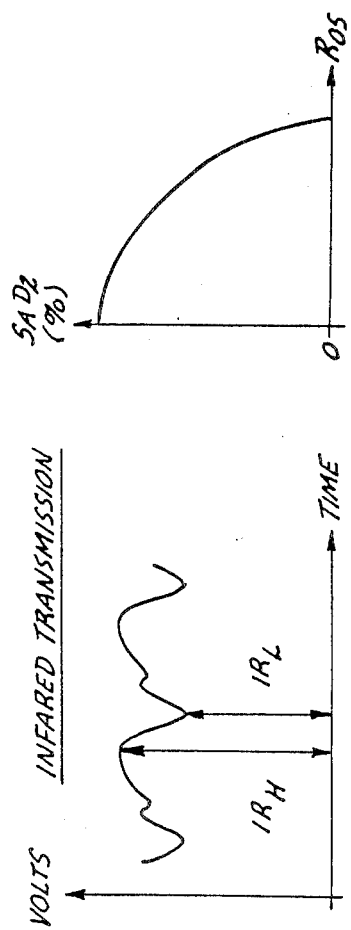
Fig. 7.
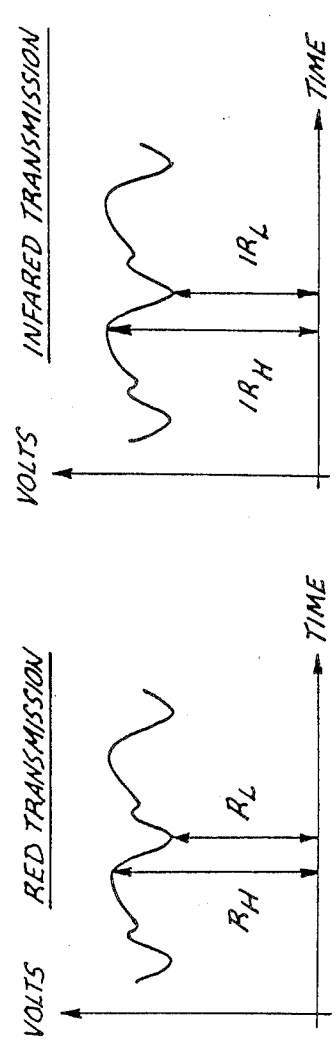
Fig. 9.
Fig. 10.

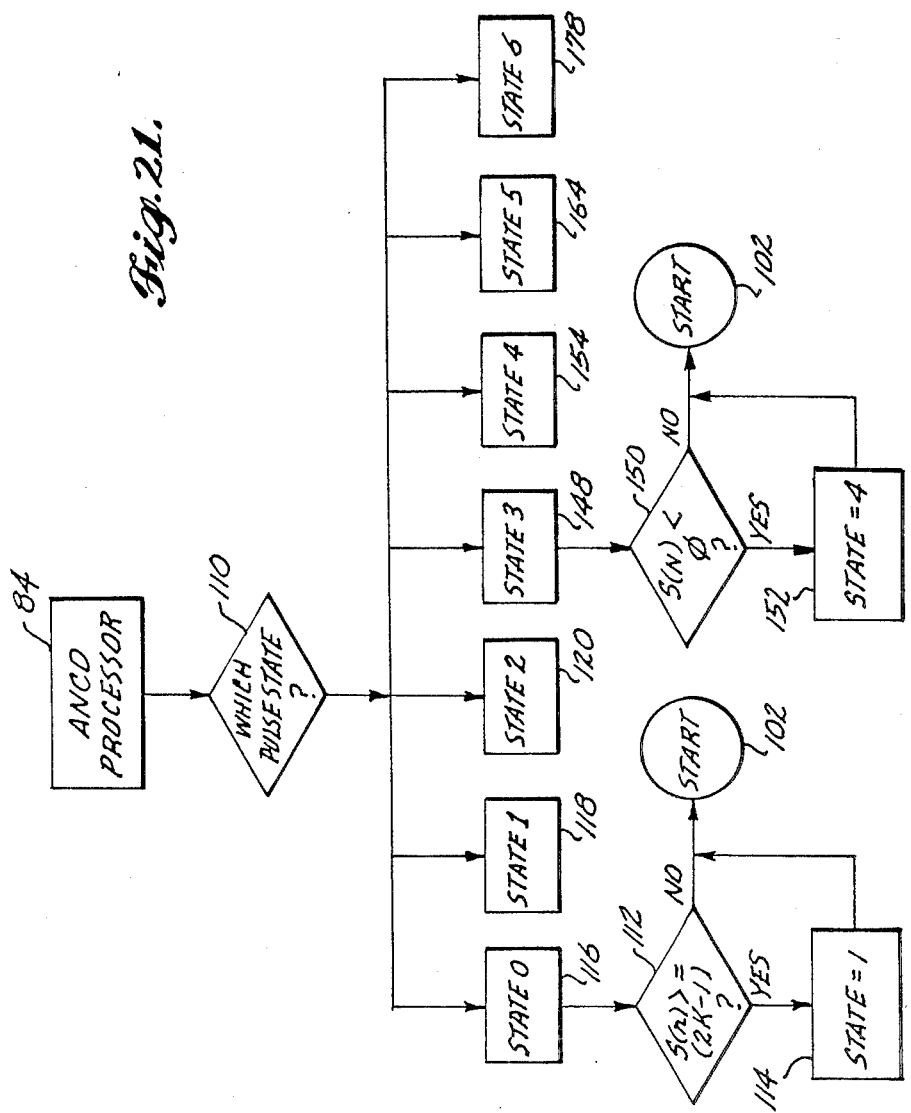

METHOD AND APPARATUS FOR PROCESSING SIGNALS USED IN OXIMETRY

BACKGROUND OF THE INVENTION

This invention relates to oximetry and, more particularly, to signal-processing techniques employed in oximetry.

The arterial oxygen saturation and pulse rate of an individual may be of interest for a variety of reasons. For example, in the operating room up-to-date information regarding oxygen saturation can be used to signal changing physiological factors, the malfunction of anaesthesia equipment, or physician error. Similarly, in the intensive care unit, oxygen saturation information can be used to confirm the provision of proper patient ventilation and allow the patient to be withdrawn from a ventilator at an optimal rate.

In many applications, particularly including the operating room and intensive care unit, continual information regarding pulse rate and oxygen saturation is important if the presence of harmful physiological conditions is to be detected before a substantial risk to the patient is presented. A noninvasive technique is also desirable in many applications, for example, when a home health care nurse is performing a routine checkup, because it increases both operator convenience and patient comfort. Pulse transmittance oximetry is addressed to these problems and provides noninvasive, continual information about pulse rate and oxygen saturation. The information produced, however, is only useful when the operator can depend on its accuracy. The method and apparatus of the present invention are, therefore, directed to the improved accuracy of such information without undue cost.

As will be discussed in greater detail below, pulse transmittance oximetry basically involves measurement of the effect arterial blood in tissue has on the intensity of light passing therethrough. More particularly, the volume of blood in the tissue is a function of the arterial pulse, with a greater volume present at systole and a lesser volume present at diastole. Because blood absorbs some of the light passing through the tissue, the intensity of the light emerging from the tissue is inversely proportional to the volume of blood in the tissue. Thus, the emergent light intensity will vary with the arterial pulse and can be used to indicate a patient's pulse rate. In addition, the absorption coefficient of oxyhemoglobin (hemoglobin combined with oxygen, $HbO_2$) is different from that of deoxygenated hemoglobin (Hb) for most wavelengths of light. For that reason, differences in the amount of light absorbed by the blood at two different wavelengths can be used to indicate the hemoglobin oxygen saturation, % $SaO_2$ (OS), which equals $([HbO_2]/([Hb]+[HbO_2])) \times 100\%$. Thus, measurement of the amount of light transmitted through, for example, a finger can be used to determine both the patient's pulse rate and hemoglobin oxygen saturation.

As will be appreciated, the intensity of light transmitted through a finger is a function of the absorption coefficient of both "fixed" components, such as bone, tissue, skin, and hair, as well as "variable" components, such as the volume of blood in the tissue. The intensity of light transmitted through the tissue, when expressed as a function of time, is often said to include a DC component, representing the effect of the fixed components on the light, and an AC pulsatile component, representing the effect that changing tissue blood volume has on the light. Because the attenuation produced by the fixed tissue components does not contain information about pulse rate and arterial oxygen saturation, the pulsatile signal is of primary interest. In that regard, many of the prior art transmittance oximetry techniques eliminate the DC component from the signal analyzed.

For example, in U.S. Pat. No. 2,706,927 (Wood) measurements of light absorption at two wavelengths are taken under a "bloodless" condition and a "normal" condition. In the bloodless condition, as much blood as possible is squeezed from the tissue being analyzed. Then, light at both wavelengths is transmitted through the tissue and absorption measurements made. These measurements indicate the effect that all nonblood tissue components have on the light. When normal blood flow has been restored to the tissue, a second set of measurements is made that indicates the influence of both the blood and nonblood components. The difference in light absorption between the two conditions is then used to determine the average oxygen saturation of the tissue, including the effects of both arterial and venous blood. As will be readily apparent, this process basically eliminates the DC, nonblood component from the signal that the oxygen saturation is extracted from.

For a number of reasons, however, the Wood method fails to provide the necessary accuracy. For example, a true bloodless condition is not practical to obtain. In addition, efforts to obtain a bloodless condition, such as by squeezing the tissue, may result in a different light transmission path for the two conditions. In addition to problems with accuracy, the Wood approach is both inconvenient and time consuming.

A more refined approach to pulse transmittance oximetry is disclosed in U.S. Pat. No. 4,086,915 (Kofsky et al.). The Kofsky et al. reference is of interest for two reasons. First, the technique employed automatically eliminates the effect that fixed components in the tissue have on the light transmitted therethrough, avoiding the need to produce bloodless tissue. More particularly, as developed in the Kofsky et al. reference from the Beer-Lambert law of absorption, the derivatives of the intensity of the light transmitted through the tissue at two different wavelengths, when multiplied by predetermined pseudocoefficients, can be used to determine oxygen saturation. Basic mathematics indicate that such derivatives are substantially independent of the DC component of the intensity. The pseudocoefficients are determined through measurements taken during a calibration procedure in which a patient first respires air having a normal oxygen content and, later, respires air of a reduced oxygen content. As will be appreciated, this calibration process is at best cumbersome.

The second feature of the Kofsky et al. arrangement that is of interest is its removal of the DC component of the signal prior to being amplified for subsequent processing. More particularly, the signal is amplified to allow its slope (i.e., the derivative) to be more accurately determined. To avoid amplifier saturation, a portion of the relatively large DC component of the signal is removed prior to amplification. To accomplish this removal, the signal from the light detector is applied to the two inputs of a differential amplifier as follows. The signal is directly input to the positive terminal of the amplifier. The signal is also passed through a low-resolution A/D converter, followed by a D/A converter, before being input to the negative terminal of the amplifier. The A/D converter has a resolution of approximately 1/10 that of the input signal. For example, if the signal is at 6.3 volts, the output of the A/D converter would be 6 volts. Therefore, the output of the converter represents a substantial portion of the signal, which typically can be used to approximate the DC signal level. Combination of that signal with the directly applied detector signal at the amplifier produces an output that can be used to approximate the AC signal. As will be readily appreciated, however, the process may be relatively inaccurate because the output of the A/D converter is often a poor indicator of the DC signal.

Another reference addressed to pulse transmittance oximetry is U.S. Pat. No. 4,407,290 (Wilber). In that reference, light pulses produced by LEDs at two different wavelengths are applied to, for example, an earlobe. A sensor responds to the light transmitted through the earlobe, producing a signal for each wavelength having a DC and AC component resulting from the presence of constant and pulsatile absorptive components in the earlobe. A normalization circuit employs feedback to scale both signals so that the DC nonpulsatile components of each are equal and the offset voltages removed. Decoders separate the two signals, so controlled, into channels A and B where lowpass filters remove the DC component from each. The remaining AC components of the signals are amplified and combined at a multiplexer prior to analog-to-digital (A/D) conversion. Oxygen saturation is determined by a digital processor in accordance with the following relationship.

U.S. Pat. No. 4,167,331 (Nielson) disclose another pulse transmittance oximeter. The disclosed oximeter is based upon the principle that the absorption of light by a material is directly proportional to the logarithm of the light intensity after having been attenuated by the absorber, as derived from the Beer-Lambert law. The oximeter employs light-emitting diodes (LEDs) to produce light at red infrared wavelengths for transmission through tissue. A photosensitive device responds to the light produced by the LEDs and attenuated by the tissue, producing an output current. That output current is amplified by a logarithmic amplifier to produce a signal having AC and DC components and containing information about the intensity of light transmitted at both wavelengths. Sample-and-hold circuits demodulate the red and infrared wavelength signals. The DC components of each signal are then blocked by a series bandpass amplifier and capacitors, eliminating the effect of the fixed absorptive components from the signal. The resultant AC signal components are unaffected by fixed absorption components, such as hair, bone, tissue, skin. An average value of each AC signal is then produced. The ratio of the two averages is then used to determine the oxygen saturation from empirically determined values associated with the ratio. The AC components are also used to determine the pulse rate:

$$OS = \frac{X_1 R(\lambda_1) + X_2 R(\lambda_2)}{X_3 R(\lambda_1) + X_4 R(\lambda_2)}$$

wherein empirically derived data for the constants $X_1$, $X_2$, $X_3$ and $X_4$ is stored in the processor.

The removal of the DC component of the signal, as typically employed by prior art devices, leaves the AC pulsatile component substantially centered about zero. This makes it easier to identify the peaks in the pulsatile waveform corresponding to systole and diastole because they will have substantially the same absolute value at each pulse. When the signal being analyzed includes the slowly varying DC component, however, the change in the DC level between pulses may cause the voltage level associated with a particular feature of the pulsatile waveform to be continually increasing or decreasing. The extraction of information from a signal including both the AC and DC components is, therefore, more complicated.

In addition, it should be noted that undesirable complicating features may be present in the signal representation of the intensity of light transmitted through the tissue. For example, the blood flow in certain individuals may exhibit a secondary pressure wave following systole, known as a dicrotic notch, that causes the signal to include a pair of slope reversals that must be distinguished from the peaks associated with systole and diastole. This phenomena is not exhibited by all individuals and the morphology of the pressure wave may vary both between different individuals and during the course of monitoring the same individual. Other undesirable features to be rejected include those produced by movement of the sensor relative to the patient, 50 Hz and 60 Hz power source interference, 120 Hz fluorescent lighting interference, and electrosurgical interference.

The present invention is directed to the accurate extraction of information from such signals including both the AC and DC components in a manner substantially unaffected by the complicating factors noted above.

SUMMARY OF THE INVENTION

The invention discloses an apparatus for processing signals containing information about the pulse rate and oxygen saturation of arterial blood flowing in tissue. These signals have a relatively periodic pulsatile component superimposed upon a varying baseline component. The apparatus includes an identifier for identifying a first portion of the signal during which the sign of the signal's slope changes from positive to negative. A positive peak locater then searches the first portion of the signal to locate the point having the largest amplitude. This point is defined as the positive peak of the signal. Similarly, a second portion identifier is included to identify a second portion of the signal during which the sign of the signal's slope changes from negative to positive. A negative peak locater then examines the second portion of the signal to locate the point having the smallest amplitude. This point is defined as the negative peak of the signal. The difference in signal amplitude between the positive and negative peaks is defined as a phase amplitude.

In accordance with a particular aspect of the invention, the first portion and second portion identifiers include a derivative identifier for producing an output indicative of the first derivative of the signal with respect to time. A first marker then identifies an initial point on the signal at which the absolute value of that output crosses below a predetermined threshold. A second marker identifies the point on the signal at which the absolute value of the output first crosses back above the predetermined threshold. Preferably, the output produced by the derivative processor is the autonormalized convolution derivative of the signal determined in accordance with the relationship:

$$S(n) = \sum_{J=n-k+1}^{n+k} \text{sign}\,[V(J) - V(J-1)]$$

where
- n is the sample time for which the autonormalized convolution derivative is determined; j is a summation index;
- V(j) is the amplitude of the signal at a sample time j; and
- k is an integer used to define the range over which the samples are summed. Preferably, S(n) is determined for k equal to three.

In accordance with additional aspects of the invention, a positive slope detector is included to determine whether the slope of the signal has been positive for some predetermined time before a first portion of the signal is identified. The arrangement can be used to cooperatively produce a plurality of pairs of positive and negative peaks. A period analyzer can be included to determine the time interval occurring between the positive and negative peaks of the sample and an additional analyzer included to produce an output of the pulse rate and oxygen saturation from the positive and negative peak information.

In accordance with another aspect of the invention, a rejection apparatus is included that rejects positive and negative peaks when those peaks fail to satisfy a selection criterion. For example, the criterion may include a pulse amplitude template defining an allowable pulse amplitude range. Thus, when the pulse amplitude computed for the signal is outside of this allowable range, the positive and negative peaks producing that pulse amplitude are rejected. The allowable pulse amplitude range may be adjustable and initialized at a predetermined level. Preferably, the range is increased in proportion to the pulse amplitude when the pulse amplitude is outside of the range and decreased in proportion to the pulse amplitude when the pulse amplitude is within the allowable range. A comparator may also be included for comparing the average of the pulse amplitudes determined at a first and third pulse with an average determined at a second and fourth pulse.

The rejection criterion may also include a systolic interval template. This template defines an allowable systolic interval range for comparison to the time interval between the positive and negative peaks. If that systolic interval is outside of the allowable systolic interval range, the positive and negative peaks from which the systolic interval is determined are rejected. Preferably, the allowable systolic interval range is adjustable and initialized at a predetermined level. The allowable range may be increased in proportion to the systolic interval when the systolic interval is outside of the allowable range and decreased in proportion to the systolic interval when the systolic interval is within the allowable range.

As will be readily appreciated, the disclosed invention also is directed to the methods employed by the apparatus described above and in its broadest formulation includes the steps of identifying a first portion of the signal, during which the sign of the signal's slope changes from positive to negative, and locating the point along the first portion of the signal having the largest amplitude. Then a second portion of the signal is identified during which the sign of the signal's slope changes from negative to positive and the point along the second portion of the signal having the smallest amplitude is located. In this manner, positive and negative peaks are defined having a pulse amplitude defined therebetween.

BRIEF DESCRIPTION OF THE DRAWINGS

The invention can best be understood by reference to the following portion of the specification, taken in conjunction with the accompanying drawings in which:

FIG. 4 is a graphical comparison of the incident light intensity to the emergent light intensity as modeled in FIGS. 2;

FIG. 5 is a graphical comparison of the specific absorption coefficients for oxygenated hemoglobin and deoxygenated hemoglobin as a function of the wavelength of light transmitted therethrough;

FIG. 7 is a graphical comparison of empirically derived oxygen saturation measurements related to a variable that can be measured by the oximeter;

FIG. 9 is a graphical plot as a function of time of the transmission of light at the red wavelength through the finger;

FIG. 10 is a graphical plot as a function of time of the transmission of infrared light through the finger;

FIGS. 21 through 25 are more detailed block diagrams of the peak processor block shown in FIG. 15;

DETAILED DESCRIPTION

Figure 1:
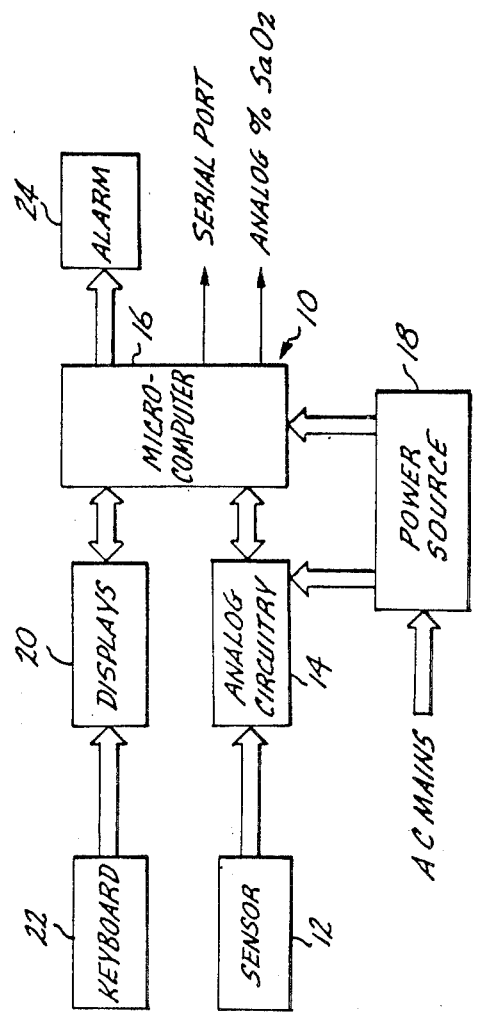
FIG. 1 is a block diagram of an oximeter including a sensor, input/output (I/O) circuit, microcomputer, alarm, displays, power supply, and keyboard.

Referring to the overall system block diagram shown in FIG. 1, a pulse transmittance oximeter 10 employing this invention includes a sensor 12, input/output (I/O) circuit 14, microcomputer 16, power source 18, display 20, keyboard 22 and alarm 24. Before discussing these elements in detail, however, an outline of the theoretical basis of pulse transmittance oximetry as practiced by the oximeter of FIG. 1 is provided.

An understanding of the relevant theory begins with a discussion of the Beer-Lambert law. This law governs the absorption of optical radiation by homogeneous absorbing media and can best be understood with reference to FIGS. 2 and 3 in the following manner.

Figure 2:
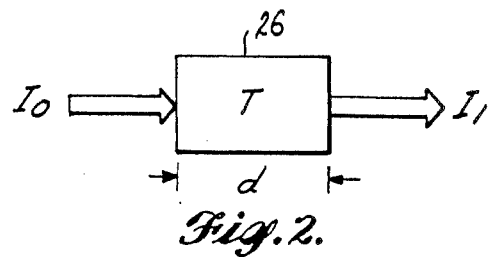
FIG. 2 is a block diagram illustrating the transmission of light through an absorptive medium.
Figure 3:
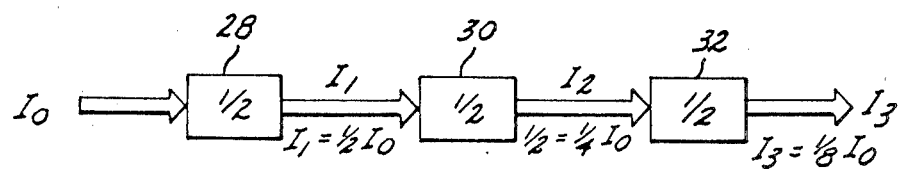
FIG. 3 is a block diagram illustrating the transmission of light through the absorptive medium of FIG. 2, wherein the medium is broken up into elemental components.

As shown in FIG. 2, incident light having an intensity $I_0$ impinges upon an absorptive medium 26. Medium 26 has a characteristic absorbance factor A that indicates the attenuating affect medium 26 has on the incident light. Similarly, a transmission factor T for the medium is defined as the reciprocal of the absorbance factor $1/A$. The intensity of the light $I_1$ emerging from medium 26 is less than $I_0$ and can be expressed functionally as the product $TI_0$. With medium 26 divided into a number of identical components, each of unit thickness (in the direction of light transmission) and the same transmission factor T, the effect of medium 26 on the incident light $I_0$ is as shown in FIG. 3.

There, medium 26 is illustrated as consisting of three components 28, 30, and 32. As will be appreciated, the intensity $I_1$ of the light emerging from component 28 is equal to the incident light intensity $I_0$ multiplied by the transmission factor T. Component 30 has a similar effect on light passing therethrough. Thus, because the light incident upon component 30 is equal to the product $TI_0$, the emergent light intensity $I_2$ is equal to the product $TI_1$ or $T^2I_0$. Component 32 has the same effect on light and, as shown in FIG. 3, the intensity of the emergent light $I_3$ for the entire medium 26 so modeled is equal to the product $TI_2$ or $T^3I_0$. If the thickness d of medium 26 is n unit lengths, it can be modeled as including n identical components of unit thickness. It will then be appreciated that the intensity of light emerging from medium 26 can be designated $I_n$ and the product is equal to $T^nI_0$. Expressed as a function of the absorbance constant A, $I_n$ can also be written as the product $(1/A^n)I_0$.

From the preceding discussion, it will be readily appreciated that the absorptive effect of medium 26 on the intensity of the incident light $I_0$ is one of exponential decay. Because A may be an inconvenient base to work with, $I_n$ can be rewritten as a function of a more convenient base, b by recognizing that $A^n$ is equal to $b^{\alpha n}$, where $\alpha$ is the absorbance of medium 26 per unit length. The term $\alpha$ is frequently referred to as the relative extinction coefficient and is equal to $\log_b A$.

Given the preceding discussion, it will be appreciated that the intensity of the light $I_n$ emerging from medium 26 can be expressed in base 10 (where $\alpha = \alpha_1$) as $I_0 10^{-\alpha_1 n}$, or in base e (where $e = \alpha_2$) as $I_0 e^{-\alpha_2 n}$. The effect that the thickness of medium 26 has on the emergent light intensity $I_n$ is graphically depicted in FIG. 4. If the light incident upon medium 26 is established as having unit intensity, FIG. 4 also represents the transmission factor T of the entire medium as a function of thickness.

The disucssion above can be applied generally to the medium 26 shown in FIG. 2 to produce:

$$I_1 = I_0 e^{-\alpha d} \qquad (1)$$

where $I_1$ is the emergent light intensity, $I_0$ is the incident light intensity, $\alpha$ is the absorbance coefficient of the medium per unit length, d is the thickness of the medium in unit lengths, and the exponential nature of the relationship has arbitrarily been expressed in terms of base e. Equation (1) is commonly referred to as the Beer-Lambert law of exponential light decay through a homogeneous absorbing medium.

With this basic understanding of the Beer-Lambert law, a discussion of its application to the problems of pulse rate and hemoglobin oxygen saturation measurement is now presented. As shown in FIG. 5, the asorption coefficients for oxygenated and deoxygenated hemoglobin are different at every wavelength, except an isobestic wavelength. Thus, it will be appreciated that if a person's finger is exposed to incident light and the emergent light intensity measured, the difference in intensity between the two, which is the amount of light absorbed, contains information relating to the oxygenated hemoglobin content of the blood in the finger. The manner in which this information is extracted from the Beer-Lambert law is discussed below. In addition, it will be appreciated that the volume of blood contained within an individual's finger varies with the individual's pulse. Thus, the thickness of the finger also varies slightly with each pulse, creating a changing path length for light transmitted through the finger. Because a longer lightpath allows additional light to be absorbed, time-dependent information relating to the difference between the incident and emergent light intensities can be used to determine the individual's pulse. The manner in which this information is extracted from the Beer-Lambert law is also discussed below.

As noted in the preceding paragraph, information about the incident and emergent intensities of light transmitted through a finger can be used to determine oxygen saturation and pulse rate. The theoretical basis for extracting the required information, however, is complicated by several problems. For example, the precise intensity of the incident light applied to the finger is not easily determined. Thus, it may be necessary to extract the required information independently of the intensity of the incident light. Further, because the changing volume of blood in the finger and, hence, thickness of the lightpath therethrough, are not exclusively dependent upon the individual's pulse, it is desirable to eliminate the changing path length as a variable from the computations.

Figure 6:
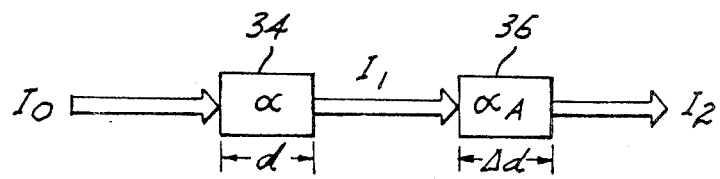
FIG. 6 is a block diagram illustrating the transmission of light through a block model of the components of a finger.

The manner in which the Beer-Lambert law is refined to eliminate the incident intensity and path length as variables is as follows. With reference to FIG. 6, a human finger is modeled by two components 34 and 36, in a manner similar to that shown in FIG. 3. Baseline component 34 models the unchanging absorptive elements of the finger. This component includes, for example, bone, tissue, skin, hair, and baseline venous and arterial blood and has a thickness designated d and an absorbance $\alpha$.

Pulsatile component 36 represents the changing absorptive portion of the finger, the arterial blood volume. As shown, the thickness of this component is designated $\Delta d$, representing the variable nature of the thickness, and the absorbance of this arterial blood component is designated $\alpha_A$ representing the arterial blood absorbance.

As will be appreciated from the earlier analysis with respect to FIG. 3, the light $I_1$ emerging from component 34 can be written as a function of the incident light intensity $I_0$ as follows:

$$I_1 = I_0 e^{-\alpha d} \tag{2}$$

Likewise, the intensity of light $I_2$ emerging from component 36 is a function of its incident light intensity $I_1$, and:

$$ti\ I_2 = I_1 e^{-\alpha_A \Delta d} \tag{3}$$

Substitution of the expression for $I_1$ developed in equation (2) for that used in equation (3), when simplified, results in the following expression for the intensity $I_2$ of light emerging from the finger as a function of the intensity of light $I_0$ incident upon the finger:

$$I_2 = I_0 e^{-[\alpha d + \alpha_A \Delta d]} \tag{4}$$

Because our interest lies in the effect on the light produced by the arterial blood volume, the relationship $I_2$ and $I_1$ is of particular interest. Defining the change in transmission produced by the arterial component 36 as $T_{\Delta A}$, we have:

$$T_{\Delta A} = \frac{I_2}{I_1} \tag{5}$$

Substituting the expressions $I_1$ and $I_2$ obtained in equations (2) and (3), respectively, equation (5) becomes:

$$T_{\Delta A} = \frac{I_0 e^{-[\alpha d + \alpha_A \Delta d]}}{I_0 e^{-\alpha d}} \tag{6}$$

It will be appreciated that the $I_0$ term can be cancelled from both the numerator and denominator of equation (6), thereby eliminating the input light intensity as a variable in the equation. With equation (6) fully simplified, the change in arterial transmission can be expressed as:

$$T_{\Delta A} = e^{-\alpha_A \Delta d} \tag{7}$$

A device employing this principle of operation is effectively self-calibrating, being independent of the incident light intensity $I_0$.

At this point, a consideration of equation (7) reveals that the changing thickness of the finger, $\Delta d$, produced by the changing arterial blood volume still remains as a variable. The $\Delta d$ variable is eliminated in the following manner. For convenience of expression, the logarithms of the terms in equation (7) are produced with respect to the same base originally employed in equation (1). Thus, equation (7) becomes:

$$\ln T_{\Delta A} = \ln(e^{-\alpha_A \Delta d}) = -\alpha_A \Delta d \tag{8}$$

A preferred technique for eliminating the $\Delta d$ variable utilizes information drawn from the change in arterial transmission experienced at two wavelengths.

The particular wavelengths selected are determined in part by consideration of a more complete expression of the arterial absorbance $\alpha_A$:

$$\alpha_A = (\alpha_{OA})(OS) - (\alpha_{DA})(1 - OS) \tag{9}$$

where $\alpha_{OA}$ is the oxygenated arterial absorbance, $\alpha_{DA}$ is the deoxygenated arterial absorbance, and OS is the hemoglobin oxygen saturation of the arterial blood volume. As will be appreciated from FIG. 6, $\alpha_{OA}$ and $\alpha_{DA}$ are substantially unequal at all light wavelengths in the red and near-infrared wavelength regions except for an isobestic wavelength occurring at approximately 805 nanometers. With an arterial oxygen saturation OS of approximately 90 percent, it will be appreciated from equation (9) that the arterial absorbance $\alpha_A$ is 90 percent attributable to the oxygenated arterial absorbance $\alpha_{OA}$ and 10 percent attributable to the deoxygenated arterial absorbance $\alpha_{DA}$. At the isobestic wavelength, the relative contribution of these two coefficients to the arterial absorbance $\alpha_A$ is of minimal significance in that both $\alpha_A$ and $\alpha_{DA}$ are equal. Thus, a wavelength roughly approximating the isobestic wavelength of the curves illustrated in FIG. 5 is a convenient one for use in eliminating the change in finger thickness $\Delta d$ attributable to arterial blood flow.

A second wavelength is selected at a distance from the approximately isobestic wavelength that is sufficient to allow the two signals to be easily distinguished. In addition, the relative difference of the oxygenated and deoxygenated arterial absorbances at this wavelength is more pronounced. In light of the foregoing considerations, it is generally preferred that the two wavelengths selected fall within the red and infrared regions of the electromagnetic spectrum.

The foregoing information, when combined with equation (8) is used to produce the following ratio:

$$\frac{\ln T_{\Delta AR}}{\ln T_{\Delta AIR}} = \frac{-\alpha_A \Delta d @ \lambda_R}{-\alpha_A \Delta d @ \lambda_{IR}} \tag{10}$$

where $T_{\Delta AR}$ equals the change in arterial transmission of light at the red wavelength $\lambda_R$ and $T_{\Delta AIR}$ is the change in arterial transmission at the infrared wavelength $\lambda_{IR}$. It will be appreciated that if the two sources are positioned at substantially the same location on the finger, the length of the lightpath through the finger is substantially the same for the light emitted by each. Thus, the change in the lightpath resulting from arterial blood flow, $\Delta d$, is substantially the same for both the red and infrared wavelength sources. For that reason, the $\Delta d$ term in the numerator and denominator of the right-hand side of operation (10) cancel, producing:

$$\frac{\ln T_{\Delta AR}}{\ln T_{\Delta AIR}} = \frac{\alpha_A @ \lambda_R}{\alpha_A @ \lambda_{IR}} \tag{11}$$

As will be appreciated, equation (11) is independent of both the incident light intensity $I_0$ and the change in the finger thickness $\Delta d$ attributable to arterial blood flow. The foregoing derivations form the theoretical basis of pulse oximetry measurement. Because of the complexity of the physiological process, however, the ratio indicated in equation (11) does not directly provide an accurate measurement of oxygen saturation. The correlation between the ratio of equation (11) and actual arterial blood gas measurements is, therefore, relied on to produce an indication of the oxygen saturation. Thus, if the ratio of the arterial absorbance at the red and infrared wavelengths can be determined, the oxygen saturation of the arterial blood flow can be extracted from independently derived, empirical calibration curves in a manner independent of $I_0$ and $\Delta d$.

For simplicity, a measured ratio $R_{OS}$ is defined from equation (11) as:

$$\text{Ratio} = R_{OS} = \frac{\alpha_A @ \lambda_R}{\alpha_A @ \lambda_{IR}} \quad (12)$$

It is this measured value for $R_{OS}$ that is plotted on the x-axis of independently derived oxygen saturation curves, as shown in FIG. 7 and discussed in greater detail below, with the hemoglobin oxygen saturation being referenced on the y-axis.

Figure 8:
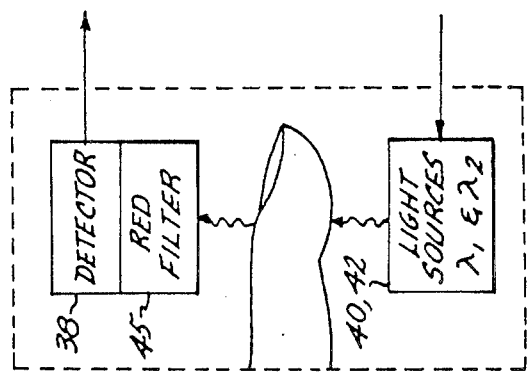
FIG. 8 is a schematic illustration of the transmission of light at two wavelengths through a finger in accordance with the invention.

Measurement of the arterial absorbances at both wavelengths is performed in the following manner. As shown in FIG. 8, a detector 38 placed on the side of a finger opposite red and infrared wavelength light sources 40 and 42 receives light at both wavelengths transmitted through the finger. As shown in FIG. 9, the received red wavelength light intensity, plotted as a function of time, varies with each pulse, and has high and low values $R_H$ and $R_L$, respectively. $R_L$ occurs substantially at systole, when arterial blood volume is at its greatest; while $R_H$ occurs substantially at distole, when the arterial blood volume is lowest. From the earlier discussion of the exponential light decay through homogeneous media, it will be appreciated that:

$$R_L = I_0 e^{-[\alpha d + \alpha_A \Delta d]} @ \lambda_R \quad (13)$$

Similarly:

$$R_H = I_0 e^{-\alpha d} @ \lambda_R \quad (14)$$

Taking the ratio of equations (13) and (14) and simplifying, we have:

$$\frac{R_L}{R_H} = \frac{I_0 e^{-[\alpha d + \alpha_A \Delta d]}}{I_0 e^{-\Delta d}} @ \lambda_R = e^{-\alpha_A \Delta d @ \lambda_R} \quad (15)$$

Taking the logarithm of both sides of equation (15) produces:

$$\ln (R_L/R_H) = \ln (e^{-\alpha_A \Delta d}) @ \lambda_R = -\alpha_A \Delta d @ \lambda_R \quad (16)$$

As will be readily appreciated, similar expression can be produced for the signals representative of the infrared wavelength light received by detector 38. Thus, the minimum light intensity passing through the finger at the infrared wavelength can be written:

$$IR_L = L_0 e^{-[\alpha d + \alpha_A \alpha d]} @ \lambda_{IR} \quad (17)$$

Similarly, the maximum light intensity emerging from the finger at the infrared wavelength can be expressed as:

$$IR_H = I_0 e^{-\alpha d} @ \lambda_{IR} \quad (18)$$

The ratio of the terms in equations (17) and (18) can be expressed as:

$$\frac{IR_L}{IR_H} = \frac{I_0 e^{-[\alpha d + \alpha_A \Delta d]}}{I_0 e^{-\Delta d}} @ \lambda_{IR} = e^{-\alpha_A \Delta d @ \lambda_{IR}} \quad (19)$$

Use of logarithms simplifies equation (19) to:

$$\ln (IR_L/IR_H) = \ln (e^{-\alpha_A \Delta d}) @ \lambda_{IR} = -\alpha_A \Delta d @ \lambda_{IR} \quad (20)$$

The ratiometric combination of equations (16) and (20) yields:

$$\frac{\ln (R_L/R_H)}{\ln (IR_L/IR_H)} = \frac{-\alpha_A \Delta d @ \lambda_R}{-\alpha_A \Delta d @ \lambda_{IR}} \quad (21)$$

Because the $\Delta d$ term in the numerator and denominator of the right-hand side of equation (21) cancel, as do the negative signs before each term, it will be appreciated that equation (21) when combined with equation (12) yields:

$$\text{Ratio} = R_{OS} = \frac{\alpha_A @ \lambda_R}{\alpha_A @ \lambda_{IR}} = \frac{\ln(R_L/R_H)}{\ln(IR_L/IR_H)} = \frac{\ln(R_H/R_L)}{\ln(IR_H/IR_L)} \quad (22)$$

Thus, by measuring the minimum and maximum emergent light intensities at both the red and infrared wavelengths ($R_L$, $R_H$, $IR_L$, $IR_H$), a value for the term $R_{OS}$ can be computed. From this, empirically derived calibration curves similar to that shown in FIG. 7 can be used to determine the oxygen saturation as described in greater detail in conjunction with the discussion of the various components of oximeter 10 that follows. As will be appreciated, the determination of oxygen saturation in this manner differs from prior art techniques, such as that disclosed by Wilber, by performing measurements based upon both the baseline and pulsatile components of the signals.

The first component of oximeter 10 to be discussed is sensor 12. The function of sensor 12 is substantially to provide the desired orientation of light sources 40 and 42, for example, light-emitting diodes (LEDs), and light detector 38 with respect to a suitable portion of a patient's body. For example, the sensor must align LEDs 40 and 42 with detector 38 in a manner such that the path of light from each LED to the detector 38 is substantially the same distance. In addition, the path must traverse a portion of the patient's body through which a usable amount of light is passed, for example, a finger, toe, earlobe, or the nasal septum. Because changes in the lightpath can significantly affect the readings taken, as noted above, the sensor must maintain the position of LEDs 40 and 42 and detector 38 with respect to the transmission path through the patient's skin at all times. Otherwise, signal fluctuations known as motion-artifact may be produced. In addition, the sensor should apply only insubstantial pressure to the patient's skin and underlying tissue. Otherwise, normal arterial blood flow upon which the pulse oximeter relies for accurate operation, may be disrupted. Finally, the sensor should be quickly attachable to the patient and should cause no discomfort.

Figure 11:
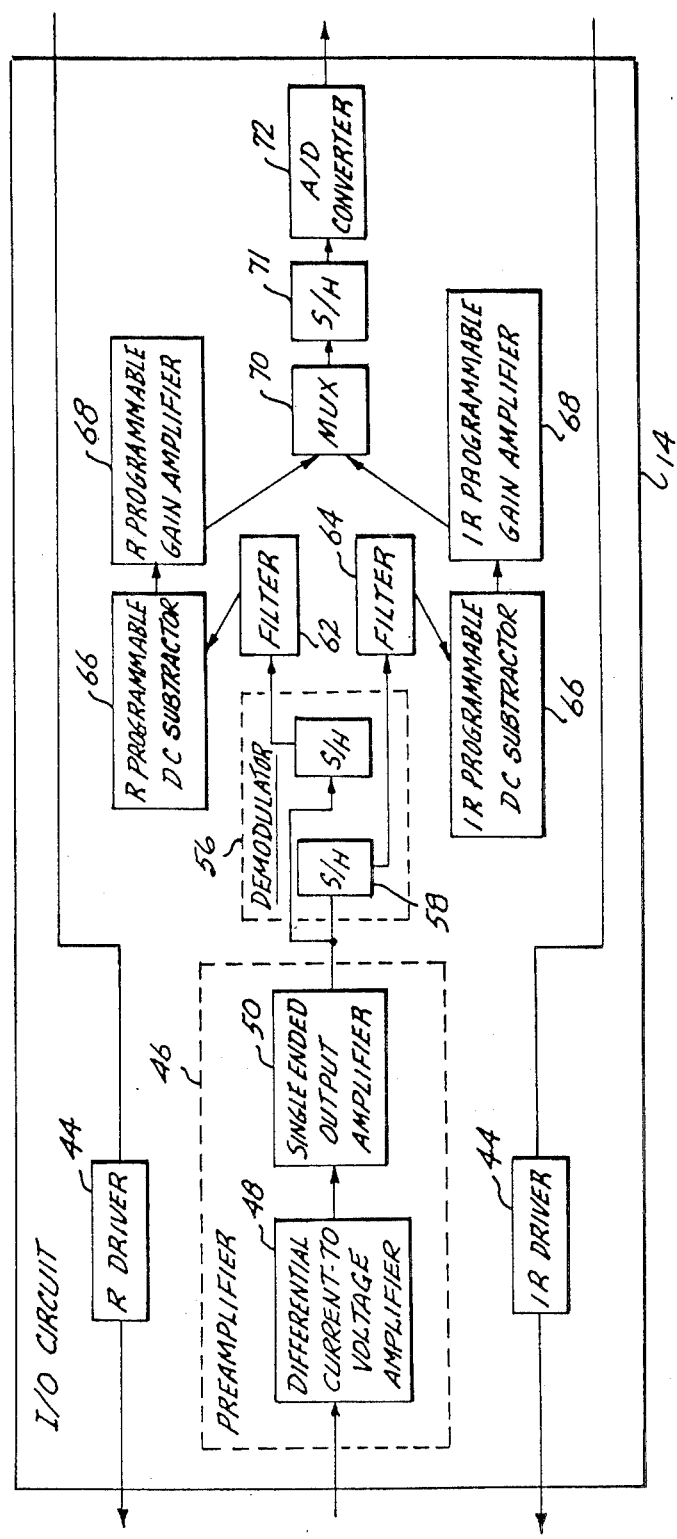
FIG. 11 is a more detailed schematic of the I/O circuit illustrated in the system of FIG. 1.

LEDs 40 and 42 are supplied with current by transistor drivers 44 located in the I/O circuit 14, as shown in FIG. 11. Drivers 44 are controlled by microcomputer 16 to produce current pulses at a 960 Hz repetition rate. The duration of each pulse is 70 microseconds and a pulse is supplied to the red wavelength LED 40 first and then to the infrared wavelength LED 42. The voltage drop across scaling resistors in the drivers 44 allows the magnitude of the current pulses to be determined and, thus, maintained in a manner described in greater detail below. LEDs 40 and 42 respond to the current pulses by producing corresponding light pulses transmitted through the finger to detector 38. Detector 38, in turn, produces a signal that includes information about the pulsatile response of the finger to the red and infrared wavelength light, intermixed at the 960 Hz LED pulse repetition rate.

In a preferred embodiment of the invention, a red optical filter 45 interrupts the lightpath between the LEDs 40 and 42 and the detector 38, as shown in FIG. 8. Preferably, filter 45 is a Kodak No. 29 wratten gel filter. Its function is to eliminate the influence of fluorescent light flicker on the oxygen saturation determination made. As will be appreciated, although the body of sensor 12 may be made of an opaque material that blocks a significant portion of the ambient light, some ambient light may still reach detector 38. Light from the sun and incandescent lamps is substantially continuous. Fluorescent lighting, on the other hand, includes alternating energized and denergized intervals that form a visually imperceptible flicker. The frequency of the fluorescent light flicker is such that it might influence the signal produced by detector 38 in response to light received from LED 40 at the red wavelength. Thus, the red optical filter 45 is placed over the detector 38 and filters out any fluorescent light present, eliminating the effect its flicker might have on the oxygen saturation determination made.

Figure 12:
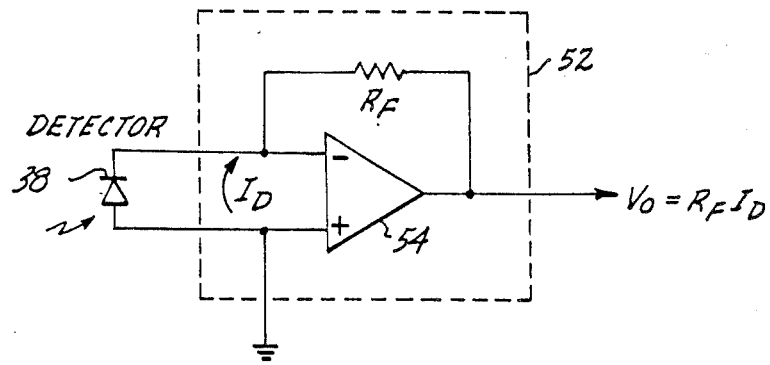
FIG. 12 is a schematic diagram of a conventional current-to-voltage amplifier circuit.

At the I/O circuit 14, the signal from detector 38 is received by a preamplifier 46. In a preferred embodiment, preamplifier 46 includes a differential current-to-voltage amplifier 48 and a single-ended output amplifier 50. To understand the advantages of using the differential amplifier 48, it may first be helpful to consider the operation of a conventional current-to-voltage amplifier as shown in FIG. 12. As shown, a current-to-voltage amplifier 52 is substantially comprised of an operational amplifier 54 and gain determination resistor $R_F$. With a detector 38 connected to the inputs of the amplifier as shown, a current $I_D$ is input to the amplifier upon the detection of suitable wavelength light. The output of amplifier 52 is designated $V_0$ and, as will be appreciated, is equal to the product of the detector current $I_D$ and the gain determination resistor $R_F$. The primary problem with such a construction is that it also amplifies the external interference noise produced, making the signal extracted accurate.

Figure 13:
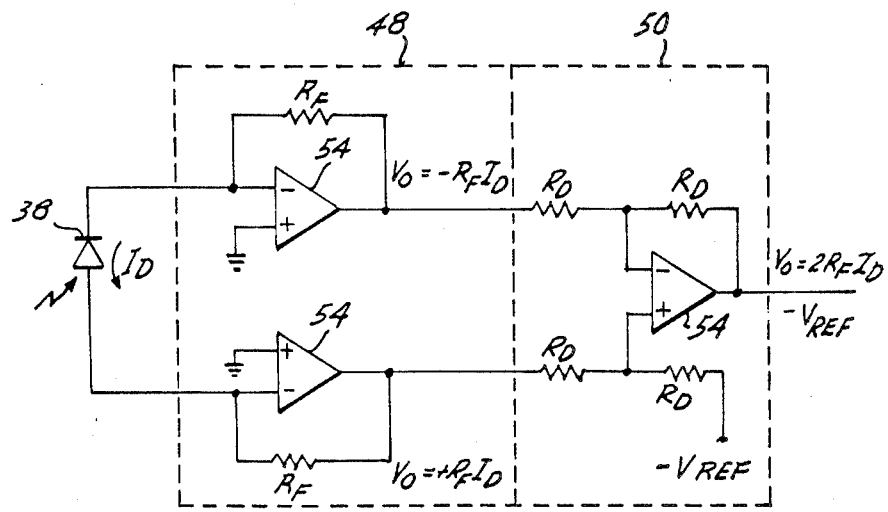
FIG. 13 is a schematic diagram of a differential current-to-voltage preamplifier circuit included in the I/O circuit of FIG. 1.

Adoption of the differential current-to-voltage amplifier 48, when combined with the single-ended output amplifier 50 as shown in FIG. 13, however, eliminates this problem. As shown, the differential amplifier 48 produces positive and negative versions of the output, the absolute value of each version being equal to the product of the gain determination resistance $R_F$ and the detector current $I_D$. These outputs are then supplied to the single-ended output amp 50, which provides unity gain, thus producing an output signal having a magnitude that is twice that of the inputs. An advantage of this arrangement is that external interference noise is cancelled at the single-ended output amplifier 50 by the opposing signs of the two transimpedance amplifier outputs. In addition, twice the signal is produced with the current noise only increasing by a magnitude of 1.414. Therefore, an improved signal-to-noise ratio results.

At this point, the mixed signal indicative of the red and infrared wavelength responses of detector 38 has been amplified and is input to a demodulator 56 to extract the red pulsatile and infrared pulsatile waveforms shown in FIGS. 9 and 10. In a preferred arrangement, the demodulator 56 includes a sample-and-hold (S/H) circuit 60 that responds to the detector signal produced in response to red wavelength light and a sample-and-hold (S/H) circuit 58 that responds to the infrared wavelength response of detector 38. The timing of circuits 58 and 60 is controlled so that each circuit samples the signal input to demodulator 56 during the portion of the signal corresponding to the wavelength to which it responds. In this manner, two signals are reconstructed from the single input to demodulator 56. As noted above, these signals correspond to the red pulsatile signal and infrared pulsatile signals shown in FIGS. 9 and 10.

The outputs of circuits 58 and 60 are next input to lowpass filters 62 and 64. As will be appreciated, if the signals are to be accurately reconstructed through sampling, the sample rate must exceed the Nyquist rate of twice the maximum frequency component in the signals. By removing high-frequency components of the signals, lowpass filters 62 and 64 thus allow the signals to be accurately sampled at a lower sample rate. In a preferred embodiment, the "red" lowpass filter 62 and "infrared" lowpass filter 64 each include two stages. The first stage of each filter utilizes a fifth-order, monolithic integrated circuit switched capacitor filter because of its low cost and relatively small physical size. Since both the "red" and "infrared" signals pass through identical first-stage filters, their gain and phase frequency responses are matched. The second stage of each filter is a second-order Bessel filter having a slightly higher roll-off frequency than the first stage. This ensures that the first-stage filter is the dominant filter of the two-stage combination, producing the desired filtering accuracy. The second stage then filters the switching noise from the first-stage output.

The filtered red and infrared pulsatile signals are next prepared for conversion and transmission to the microcomputer 16. As will be discussed in greater detail below, this process involves the use of a programmable DC subtractor or offset 66, followed by a programmable gain amplifier 68 having a gain range from approximately one to 256. The appropriately processed signals are combined at multiplexer 70, sampled and held at 71, and converted to digital form and demultiplexed by A/D converter 72 for transmission to microcomputer 16.

Before a more complete discussion of the operation of programmable subtractor 66, programmable gain amplifier 68, multiplexer 70, S/H 71, and A/D converter 72 is provided, several details regarding the signals to be transferred to microcomputer 16 should be noted. For example, as shown in FIGS. 9 and 10, the signal produced by detector 30 in response to light at each wavelength includes components that, for convenience, are termed baseline and pulsatile. The baseline component approximates the intensity of light received at detector 38 when only the "fixed" nonpulsatile absorptive component is present in the finger. This component of the signal is relatively constant over short intervals but does vary with nonpulsatile physiological changes or system changes, such as movement of sensor 12 on the finger.

Over a relatively long interval this baseline component may vary significantly. As will be appreciated, the magnitude of the baseline component at a given point in time is substantially equal to the level identified in FIG. 9 as $R_H$. For convenience, however, the baseline component may be thought of as the level indicated by $R_L$, with the pulsatile component varying between the values for $R_H$ and $R_L$ over a given pulse. That pulsatile component is attributable to light transmission changes through the finger resulting from blood volume changes in the finger during a cardiac pulse. Typically, the pulsatile component may be relatively small in comparison to the baseline component and is shown out of proportion in FIGS. 9 and 10.

The determination of $R_{OS}$ in accordance with equation (22) requires accurately measured values for both the baseline and pulsatile signal components. Because the pulsatile components are smaller, however, greater care must be exercised with respect to the mesurement of these components. As will be readily appreciated, if the entire signal shown in FIGS. 9 and 10, including the baseline and pulsatile components, was amplified and converted to a digital format for use by the microcomputer 16, a great deal of the accuracy of the conversion would be wasted because a substantial portion of the resolution would be used to measure the baseline component. For example, with an A/D converter employed having an input range of between +10 and −10 volts, a signal having a baseline component referenced to −10 volts that is four times that of the pulsatile component can be amplified until the baseline component is represented by a 16-volt difference and the pulsatile signal represented by a 4-volt difference. With a 12-bit A/D converter 72, the total signal can be resolved into 4096 components. Therefore, the number of incremental levels representing the pulsatile signal would be approximately 819. If, on the other hand, the baseline component is removed prior to the conversion, the gained pulsatile signal could be resolved into 4096 intervals, substantially improving accuracy.

Figure 14:
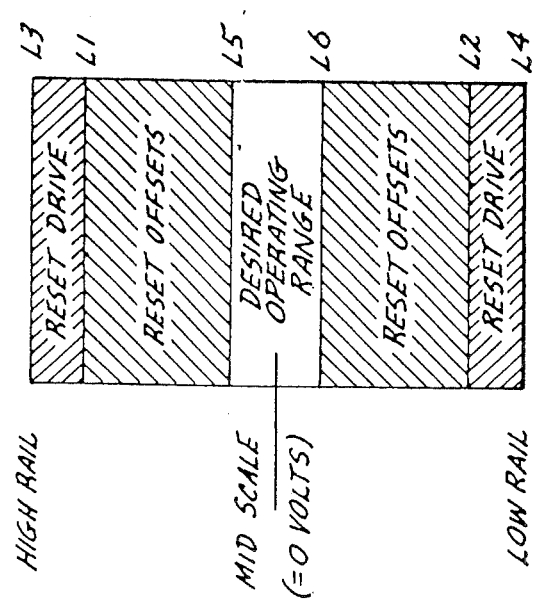
FIG. 14 is a graphical representation of the possible ranges of the I/O circuit output showing the desired response of the I/O circuit and microcomputer at each of the various possible ranges.

The disclosed invention employs this technique, as the first half of a construction-reconstruction process, in the manner schematically outlined in FIG. 14. As shown, an input signal $V_1$ (corresponding to the signals shown in FIGS. 9 and 10) is received from each filter 62 and 64. $V_1$ includes both the baseline and pulsatile components discussed above. As will be described, subsequent operations upon $V_1$ subtract off a substantial "offset voltage" portion of the baseline component, then gain up the remaining substantially pulsatile signal for conversion by A/D converter 72. A digital reconstruction of the original signal is then produced by reversing the process, wherein digitally provided information allows the gain to be removed and the offset voltage added back. This step is necessary because the entire signal, including both the baseline and pulsatile components, is used in the oxygen saturation measurement process.

Feedback from microcomputer 16 to I/O circuit 14 also required to maintain the values for the offset voltage and driver currents at levels appropriate to produce optimal A/D converter 72 resolution. Proper control requires that the microcomputer continually analyze, and respond to, the offset voltage, driver currents, and the output of A/D converter in a manner to be described next.

Briefly, with reference to FIG. 14, thresholds L1 and L2 slightly below and above the maximum positive and negative excursions L3 and L4 allowable for the A/D converter 72 input are established and monitored by microcomputer 16 at the A/D converter output. When the magnitude of the signal input to, and output from, A/D converter 72 exceeds either of the thresholds L1 or L2, the drive currents $I_D$ are readjusted to decrease the intensity of light impinging upon the detector 38. In this manner, the A/D converter 72 is not overdriven and the margin between L1 and L3 and between L2 and L4 helps assure this, even for rapidly varying signals. An operable voltage margin for A/D converter 72 exists outside of the thresholds, allowing A/D converter 72 to continue operating while the appropriate feedback adjustments to A and $V_{OS}$ are made.

When the signal from A/D converter 72 exceeds positive and negative thresholds L5 or L6, microcomputer 16 responds by signaling the programmable subtractor 66 to increase the amount of offset voltage being subtracted. This is done through the formation and transmission of an offset code whose magnitude is dependent upon the level of the signal received from converter 72.

The manner in which the various thresholds are established, and the relationship of the offset codes to the signal received, can be altered to produce substantially any form of control desired. Thus, the arrangement shown in FIG. 14 is illustrative only and represents the currently preferred embodiment. As noted, the instructions for the software that controls the signal construction-reconstruction process discussed above are stored in EPROM 78 of microcomputer 16. Similarly, the manner in which values for $R_H$, $R_L$, $IR_H$, $IR_L$, and the signal period are extracted from the output of A/D converter 72 is determined pursuant to software stored in EPROM 78. This software is discussed below in connection with FIG. 15, which provides, in part, an overall block diagram of the software.

Figure 15:
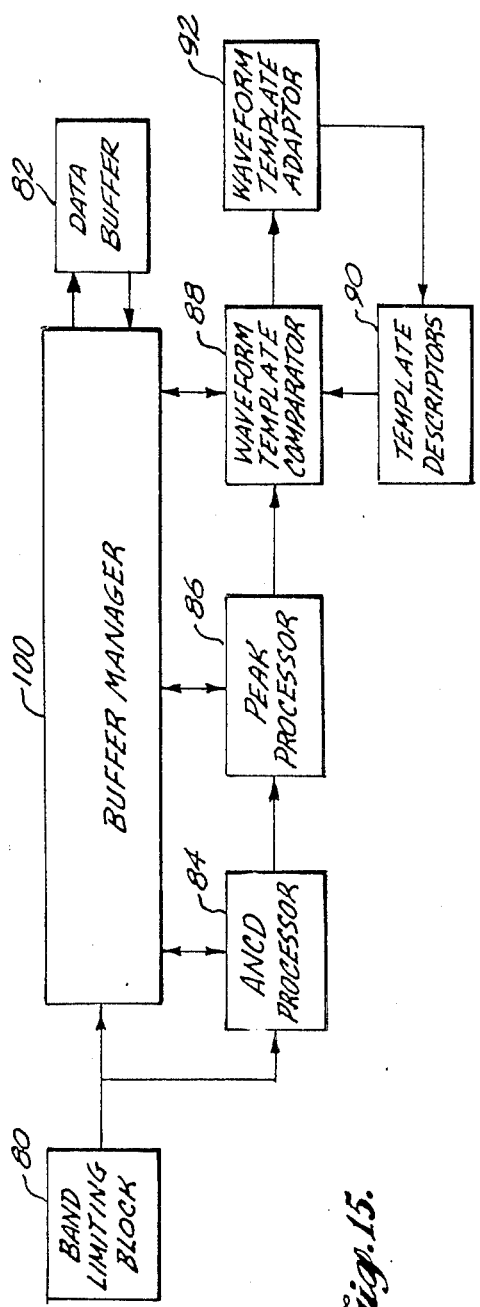
FIG. 15 is a block diagram of a portion of the signal processing software included in the microcomputer illustrated in FIG. 1, showing band-limiting, data buffer, autonormalized convolution derivative (ANCD) processor, peak processor, waveform template comparator, template adaptor, and template descriptor blocks.

Briefly, the arrangement shown in FIG. 15 includes a band-limiting block 80 that conditions the demultiplexed signals received from A/D converter 72. The resultant band-limited signals, corresponding to the light transmitted through the tissue at both wavelengths, are applied to a data buffer 82. Buffer 82 stores the signals for future analysis as described in greater detail below.

An autonormalized convolution derivative (ANCD) processor block 84 continually computes the ANCD of one of the two signals with respect to time. The ANCD is basically the sum of the signs of the signal change over a plurality of intervals related to the time at which the ANCD is determined. As will be discussed in greater detail below, the ANCD provides a reduced-information indication of the first derivative of the signal with respect to time. The ANCD is then examined by a peak processor block 86 that initially searches for a region of the signal having a sustained positive slope. With such a region detected, block 86 next begins the search for a positive peak. To accomplish this, block 86 determines when the absolute value of the ANCD falls below some predetermined threshold. Block 86 then marks the point on the waveform stored in data buffer 82 that corresponds to the threshold crossing by the ANCD.

Peak processor block 86 continues to search for a subsequent crossing of the threshold by the ANCD marking a second point on the waveform when this occurs. The portion of the waveform stored in buffer 82 between the two points is then analyzed to determine whether it includes a positive peak. When a peak is detected, a slightly expanded portion of the waveform stored in buffer 82 corresponding to the other wavelength of light is similarly examined to identify the location of its peak. Then processor block 86 returns to its analysis of the ANCD of the first signal. After a negatively sloping region of the signal is detected, a search for negative peaks is performed in a manner similar to that outlined for the positive peaks above. A test is also performed by block 86 at start-up to reject signal disturbances produced by the dicrotic notch that might otherwise be identified as positive and negative peaks.

With acceptable peaks identified, the program is advanced from peak processor block 86 to waveform template comparator block 88. Waveform template comparator block 88 compares the portion of the waveform stored in data buffer 82 that is associated with the peaks to template descriptors provided via template descriptor block 90. These descriptors basically define limits on pulse amplitude and systole duration. If a positive verification is made, the features previously identified are accepted as representative of a pulse. Otherwise, the previously identified features of interest are rejected and control of the program passes back to peak processor block 86 where the search for features of interest is restarted.

Once peak processor block 86 and waveform template comparator block 88 cooperatively identify a pulse, the waveform information corresponding to the peaks is analyzed by a waveform template adaptor block 92. Block 92 modifies the template descriptors produced by block 90 in accordance with the newly identified pulse features. The points on the waveform stored in data buffer 82 that correspond to these features are stored in the data buffer 82 by a buffer manager 100 for further processing, such as template modification and the computation of oxygen saturation.

Figure 16:
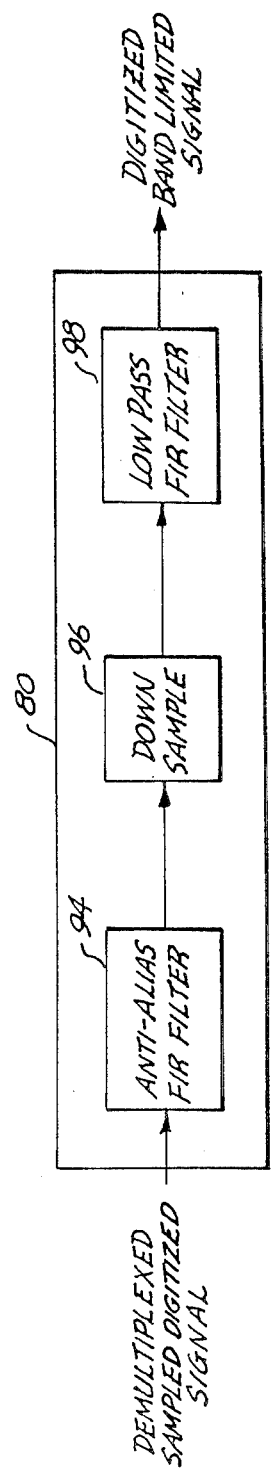
FIG. 16 is a more detailed block diagram of the band-limiting block shown in FIG. 15.

Turning now to a more detailed discussion of the various blocks shown in FIG. 15, FIG. 16 illustrates the band-limiting block 80. As noted previously, band-limiting block 80 receives demultiplexed signals from A/D converter 72 representing the intensity of light received by detector 38 at the red and infrared wavelengths. Each signal is received by a digital, anti-aliasing, finite impulse response (FIR) filter 94. This filter band-limits the oversampled signal to remove high-frequency components therein. In this manner, the signals can be subsequently down-sampled to a lower sample rate.

As implied, the filtered digital signal is sampled at a lower sampling rate (e.g., 48 Hz) at block 96. This simplifies the lowpass filtering performed by a digital FIR filter at block 98. The operation of block 98 severely limits the passband of the signal, passing only the fundamental frequency of the signal as well as a few of the harmonic terms. The result is that block 98 removes a substantial portion of the undesired 50-, 60-, and 120 Hz noise described above, as well as electrosurgical interference.

A second, and equally important function of filter 98 is to reduce the complexity of the processor block 84 required to determine the ANCD of the signal. As will be appreciated, elimination of the high-frequency components reduces the abruptness with which the signal changes, resulting in more gradual changes in the derivative or slope of the signal. These gradual changes in the first derivative are more easily identified by the ANCD processing block 84.

The signals corresponding to each wavelength, once appropriately conditioned by band-limiting block 80, are input to data buffer 82 in response to the control of buffer manager 100. Buffer manager 100 controls the bidirectional communications link between the buffered waveforms and the various processing blocks or subroutines operating upon the waveforms. By storing the raw waveforms in data buffer 82, the waveforms can be reprocessed in light of subsequently obtained information. For example, the levels associated with subsequently determined features of interest can be extracted and, ultimately, the information necessary to determine $R_{OS}$ obtained.

In addition to being stored in data buffer 82, the signal or waveform corresponding to one of the two wavelengths of light is input to the ANCD processor block 84. The function of block 84, as noted above, is to produce an indication of the first derivative or slope of the signal received. As will be readily appreciated, the slope can be used to identify a number of signal characteristics. For example, when the slope of the signal is zero, either a point of inflection or peak of the signal is indicated. Because the occurrence of a positive or negative peak also results in a slope reversal, peaks may be differentiated from inflection points by monitoring the signal slope both before and after the detection of a zero slope. Thus, the first derivative provides a convenient way to identify waveform features.

While the signal produced for analysis by peak processor block 86 can be a direct measurement of the signal slope, it is noted that not all of the information contained in the first derivative is required to determine slope reversals. In the preferred arrangement, ANCD processor block 84 uses information about the sign of the derivative to produce a normalized output, the ANCD, having a reduced-information content sufficient to discriminate peaks.

More particularly, with a sampled signal having a voltage V(n) at sample n received from block 80, an approximation to the derivative of V(n) can be expressed as:

$$dV(n)/dt \simeq V(n) - V(n-1) \quad (23)$$

With the signal sufficiently band-limited and the sample rate meeting the Nyquist criterion, normalization of the derivative by use of its sign reduces concerns that might otherwise be experienced from the use of an approximation of the derivative. Thus, equation (23) is rewritten in autonormalized form as:

$$\text{sign } [dV(n)/dt] \simeq \text{sign } [V(n) - V(n-1)] \quad (24)$$

This autonormalized approximation of the derivative provides sufficient processing of the signal V(t) to discriminate peaks from inflections in the signal, provided that the signal is a "well-behaved" function. In practice, physiological signals such as the voltage output of the photoplethysmograph are not such functions are indeed are modulated with artifacts due to noise, interference and patient motion. To enhance reliable detection of peaks in the presence of these modulations, additional processing is necessary. This can be achieved by performing the convolution of the autonormalized derivative over a number of samples about the sample of interest. As will be appreciated, the convolution of equation (24) can be expressed as:

$$S(n) = \sum_{J=n-k+1}^{n+k} \text{sign}\,[V(J) - V(J-1)] \quad (25)$$

where S(n) is the sampled approximation to the continuous ANCD; 2k is the number of samples over which the sampled signal V(j) is convolved; and, j is the summation index. It is this function S(n) that is produced by ANCD processor block 84.

The use of S(n) produces many interesting side effects, such as averaging out waveform modulations of greater frequency than the signal of interest and giving a statistical estimation of the waveform at a given sample. This statistical estimation, when used in conjunction with appropriate limits and logic, provides an easy method of discriminating peaks in the waveform. The number of samples over which the signal is convolved for each sample to be estimated must be suitable for the type of feature to be discriminated. If k is too large, the process will not be responsive to the desired feature of the signal. If k is too small, the process will indicate many false detections for undesired features of the waveform. Therefore, k must be adjusted for the sampling rate used to digitize the signal V(t) as well as for the frequency domain content of the desired features to be discriminated in the signal V(t). A value of k=3 has been found particularly suitable for the application when used in conjunction with the sampling rate defined above.

Figure 17:
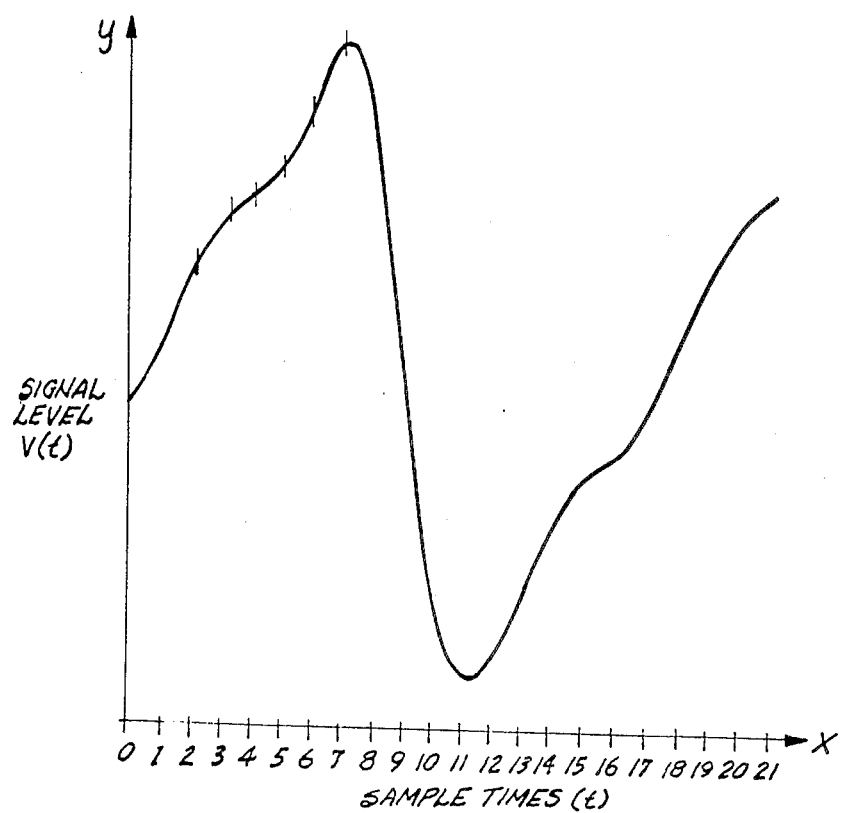
FIG. 17 is a graphical illustration of the signal received by the ANCD processor block of FIG. 15 as a function of time.
Figure 18:
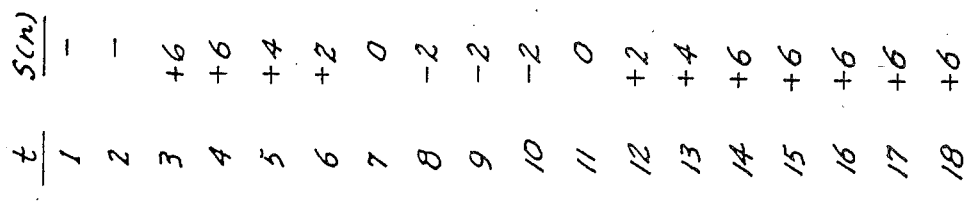
FIG. 18 is a table illustrating the output S(n) of the ANCD processor block at a plurality of sample times.

To more completely understand how S(n) is computed and used, a single pulse of an exemplary waveform is shown in FIG. 17. A plurality of sample times t are indicated on the x-axis with the signal level indicated on the y-axis. As will be appreciated, the relative scales employed on the axes of FIG. 17 are for illustrative purposes. The value of S(n) corresponding to the various samples is shown in FIG. 18. With k arbitrarily assumed to be three, the summation performed in accordance with equation (23) includes the previous three and following three sample intervals. Thus, upon start-up, a value for S(n) at time three cannot be computed until the occurrence of time six. Designating time three as the first sample of interest time n, S(n) is computed in accordance with equation (23) for a range of times extending between 0 and +6. The individual sign changes are determined by the signal level change between adjacent samples within this range. As clearly indicated from FIG. 17, each of these sign changes is positive and the sum of the sign changes is indicated as a positive six. When the sample of interest corresponds to the signal level occurring at time five, the sum computed in accordance with equation (23) includes five positive sign changes and one negative sign change. Thus, S(n) is represented as a positive four. The remaining values in FIG. 18 are computed in a similar manner.

Figure 19:
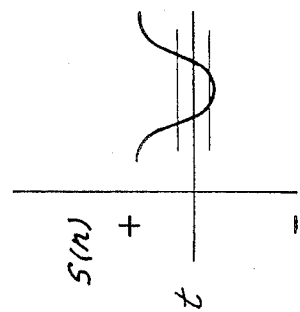
FIG. 19 is a graph representative of the output of the ANCD processor block over an interval corresponding to one pulse.

As will be readily appreciated from the foregoing discussion, as the absolute value of the magnitude of S(n) approaches zero, a point of interest on the sampled waveform is indicated. The plot of this first derivative as a function of time over a pulse similar to that idicated in FIG. 17 is shown in FIG. 19.

Figure 20:
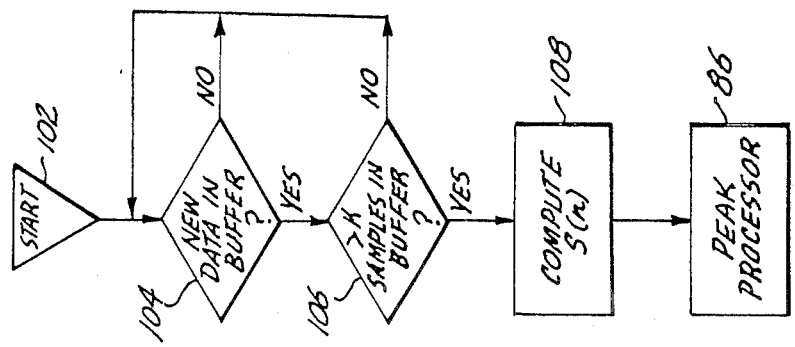
FIG. 20 is a more detailed block diagram of the ANCD processor block shown in FIG. 15.

The organization of the software instructions performed through this point is shown in block form in FIG. 20. There, the process begins with a start block 102. At block 104 a test is performed to determine whether a new data sample has been placed in buffer 82. As shown, the program will not proceed until this condition is satisfied. With new data placed in buffer 82, however, a second test is performed at block 106 during start-up to determine whether the number of samples stored in buffer 82 is greater than 2k. This test ensures that enough samples have been taken to allow S(n) to be computed. If the test is not satisfied, a return is initiated until more than 2k samples of the waveform have been taken. At that time, a value for S(n) is computed at block 108. The output of block 108 represents the ANCD of the signal at the sample point and is supplied to the peak processor block 86, which will now be described in greater detail.

Peak processor block 86 is responsible for three separate aspects of feature detection. First, block 86 locates and marks points associated with derivative sign change or inflection. Second, peak processor block 86 locates maximum and minimum peaks between the points marked. Third, the peak processor 86 is responsible for pairing up positive and negative peaks for transmission to the waveform template comparator block 88, which performs pulse detection.

As shown in greater detail in FIGS. 21 through 25, the peak processor block 86 includes seven states of operation designated zero through six. As shown in FIG. 21, peak processing begins with a test at block 110 to determine which state is to be accessed. Initially, the program is directed to state zero where the sum S(n) for the sample of interest is checked to determine whether a sustained positive slope is present. Thus, at block 112, a test is performed to determine whether S(n) is greater than or equal to 2k−1. Recalling the example illustrated in FIGS. 17 and 18, this condition is satisfied (S(n) is greater than plus five) at times three, four and fourteen through eighteen. These points clearly correspond to the sustained slope regions of the signal.

The test performed at block 112 is used to initiate the search process because a sustained positive slope provides a convenient reference point from which subsequent positive peaks can be searched. If a sustained positive slope has not been found at block 112, the program is returned to block 102 so that the next sample can be taken. This process continues until the test at block 112 indicates that a sustained positive slope has been located. At this time, the program progresses to block 114 where the peak processor state is incremented to state one. Then the program is returned to start at block 102 for the next data sample to be taken.

With the state set to one, the pulse state inquiry performed at block 110 causes the peak processor routine 86 to progress to the state one block 118 upon its next execution. The state one block or subroutine 118 is shown in greater detail in FIG. 22. Its function is to mark the beginning of a possible feature of interest following the sustained positive slope section of the waveform stored in data buffer 82. Thus, at block 120, a test is performed to determine whether the absolute value of S(n) is less than some predetermined constant relating to the feature to be detected. As will be appreciated from FIG. 19, when the test of block 120 is satisfied, an impending point of interest on the waveform stored in data buffer 82 is indicated. If the outcome of block 120 is false, the flow is redirected to block 102 where another sample can be obtained. The peak processor state is not incremented and, the next time the peak processor 86 is accessed, block 110 will cause the state one subroutine 118 to be performed again.

When the outcome of block 120 is true at some time n1, an impending point of interest is indicated and the subroutine progresses to block 122. There, a timer is zeroed and started for use in determining whether the potential feature of interest changes slope too slowly to be acceptable. For example, if the absolute value of S(n) remains below the threshold for a time in excess of some predetermined limit, the waveform located in buffer 82 may not accurately represent the transmission characteristics of the tissue and blood being analyzed. Likewise, it may be that a slowly changing portion of the waveform has been detected, making it difficult to precisely identify a peak.

With the timer started at block 122, the program progresses to block 124 where the ANCD S(n1) at the time n1 is recorded and the corresponding point on the waveform stored in data buffer 82 is marked. The peak processor state is then incremented to state two of block 126 before being returned to the start at block 102.

At this point, with the peak processor state set to state two, a sustained positive slope has been detected that is followed by a possible inflection point or peak. The manner in which the state two subroutine 128 continues to process the information from ANCD processor block 84 is now discussed with reference to FIG. 23. Basically, the function of the state two subroutine is to determine when the absolute value of the ANCD S(n) goes back above the predetermined level tested in state one. It also makes sure that this change does not take longer than some predetermined time to occur and, in addition, rejects inflection points and possible negative peaks from a maximum positive amplitude search.

As shown at block 130 of the state two subroutine 128, as noted above, a test is performed to determine whether it has taken longer than some predetermined interval for the absolute value of S(n) to rise back above the threshold previously used. This task is accomplished via the timer started at block 122. If the interval has been exceeded, the program progresses to block 132 where the state is reset to zero and a new sustained positive slope region of the waveform sought. If, on the other hand, S(n) rises above the threshold before the timer interval expires, the program is progressed to block 136. There, a second point n2 on the waveform stored in data buffer 82 is marked and the indication of the ANCD of the waveform at that point S(n2) is saved.

At this point, the peak processor block 86 has identified a region over which a possible positive peak may be present. To exclude inflection points from subsequent analysis, a test is performed at block 138 to determine whether the sign of S(n) is the same at times n1 and n2. If it is, an inflection point on the positively increasing waveform is indicated and the state is reset to state one at block 140 before another sample is taken.

If the test performed at block 138 indicates that an inflection point does not exist between samples n1 and n2, however, a test is performed at block 142 to determine whether a positive peak lies between those two points. Thus, the sign of the ANCD at the first point is compared to zero. If it is greater than zero, a positive peak is indicated between n1 and n2. If the beginning slope is negative, however, block 142 indicates that a negative peak lies between samples n1 and n2 and the state is reset to one at step 140.

With a positive peak indicated, block 144 conducts a positive amplitude search on the waveform samples stored in data buffer 82 between samples times n1 and n2. The largest amplitude of the waveform between these points is then identified as the positive peak and its position recorded at block 146 where the state is set to three. As will be appreciated, this process allows a positive peak to be identified even when the comparative amplitude of previous or subsequent peaks is unknown.

Although the processing thus far described can be duplicated for the waveform corresponding to the other wavelength of light, in a preferred arrangement once the foregoing steps have been performed on the first signal, a similar positive amplitude search is performed on the other waveform stored in buffer 82. This is possible due to a substantial similarity of the waveforms for the two wavelengths of light. The search, however, is performed over a slightly greater portion of the waveform, defined by sample times n3 and n4. These sample times are conveniently established as predetermined functions of n1 and n2.

With a positive peak identified following a sustained positive slope region of the waveform, the next execution of the peak processor routine 86 causes the state three subroutine 148 to be accessed. The state three subroutine is shown in FIG. 21 and begins with a search for a negatively sloping portion of the waveform, following the positive peak detected at state two. Thus, at block 150, a test is performed to determine whether the signal S(n) representative of the ANCD of the waveform at the sample time n is less than zero. If it is, a negatively sloping portion of the waveform is indicated and the state is incremented to state four at block 152. Otherwise, a return is initiated at block 102 so that the next sample can be taken. In this condition, the state remains set at three and the slope will be again tested at the next sample.

Figure 24:
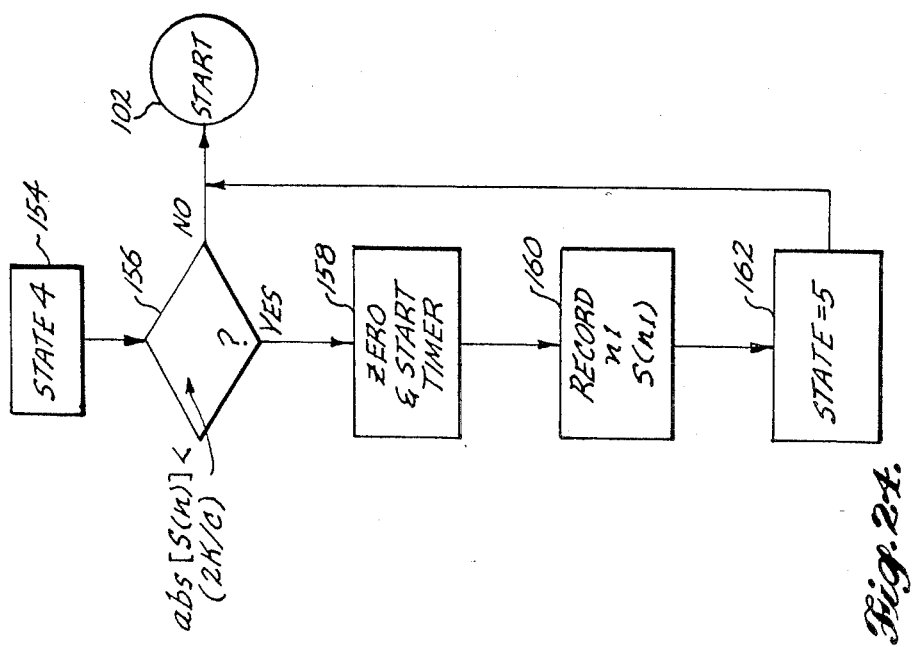
Figure 22:
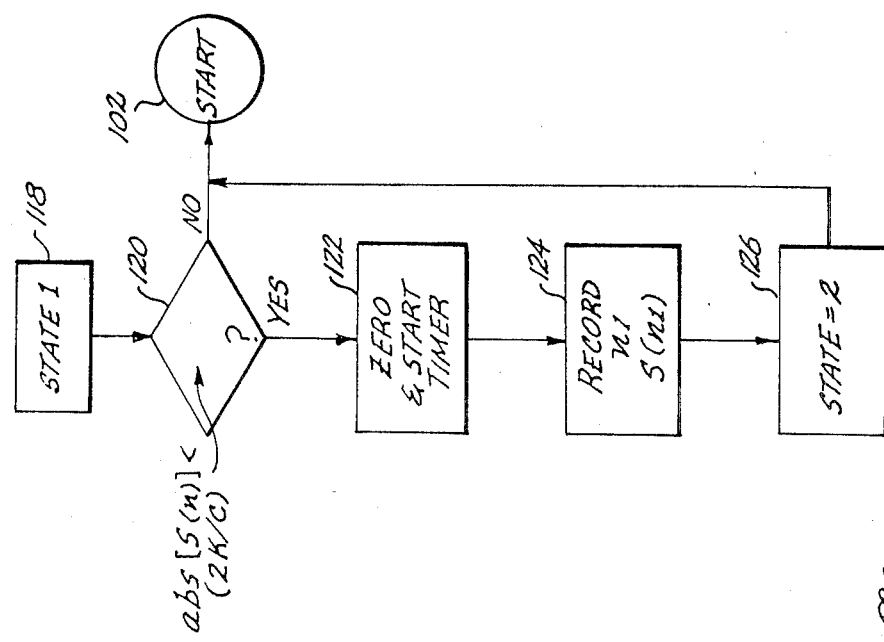
Figure 23:
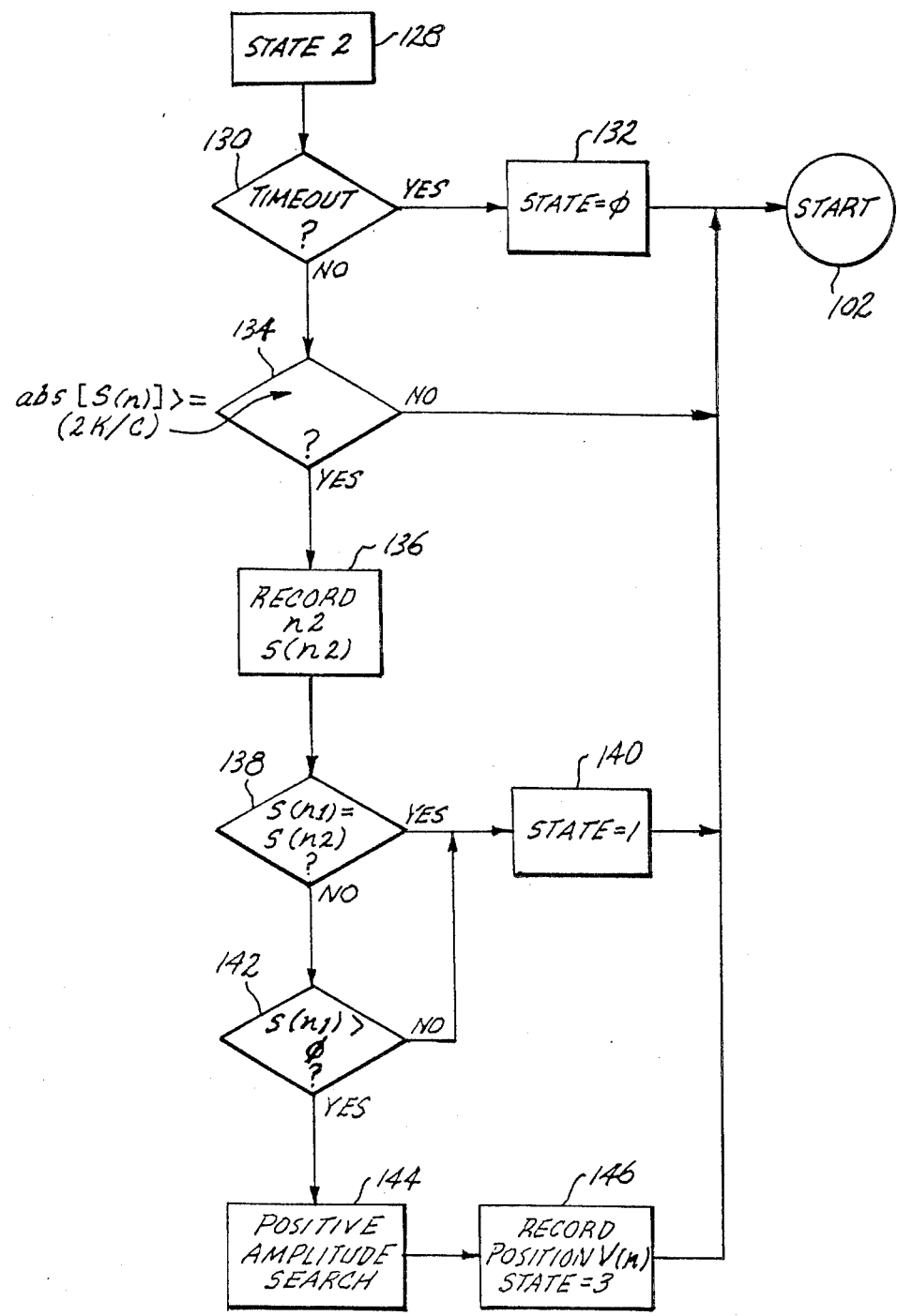

Assuming that the state has been incremented to state four, block 110 directs the program to the state four subroutine 154 on the next execution of peak processor block 86. The details of the state four subroutine 154 are shown in FIG. 24. Basically, this state begins the search for a negative peak. Thus, at block 156 a test is performed to determine whether the absolute value of S(n) has again dropped below a predetermined threshold. As will be appreciated, if this threshold has been crossed, a point of interest on the waveform stored in data buffer 82 is being approached and the program progresses to block 158. If it has not, the program is directed to start block 102 where the taking of another sample will be initiated.

At block 158, the timer is zeroed to started for subsequent use in determining whether a usable feature is present. At block 160 the sample time of this initial threshold crossing is marked as n1 and the ANCD at this point is stored as S(n1). The state is then incremented to state five at block 162 before the program is returned to start 102.

At this point, the program has detected a sustained positive slope followed by a positive peak, a negative slope, and a potential point of interest. The state five subroutine 164 then determines whether the threshold is recrossed at a second point to be marked before a predetermined timeout interval expires. Thus, at block 166 a test is performed to determine whether the predetermined timer interval has expired. If it has, and the absolute value of the signal representative of the ANCD has not returned above the predetermined threshold, or is not greater than zero, the program is directed to step 168 where the state is reset to zero and a new sample taken via the start at block 102. If, on the other hand, the absolute value of S(n) has exceeded the threshold or the sign of S(n) is positive, a negative peak lies between the sample times n1 and n2. In that case, the test at step 170 progresses the program to block 172, where the point n2 on the waveform stored in data buffer 82 is marked and the ANCD at that point S(n2) is stored. At block 174 a negative amplitude search is conducted on the waveform stored in data buffer 82 between sample times n1 and n2 with the position of the largest negative amplitude being recorded and the state incremented to a state six.

Figure 25:
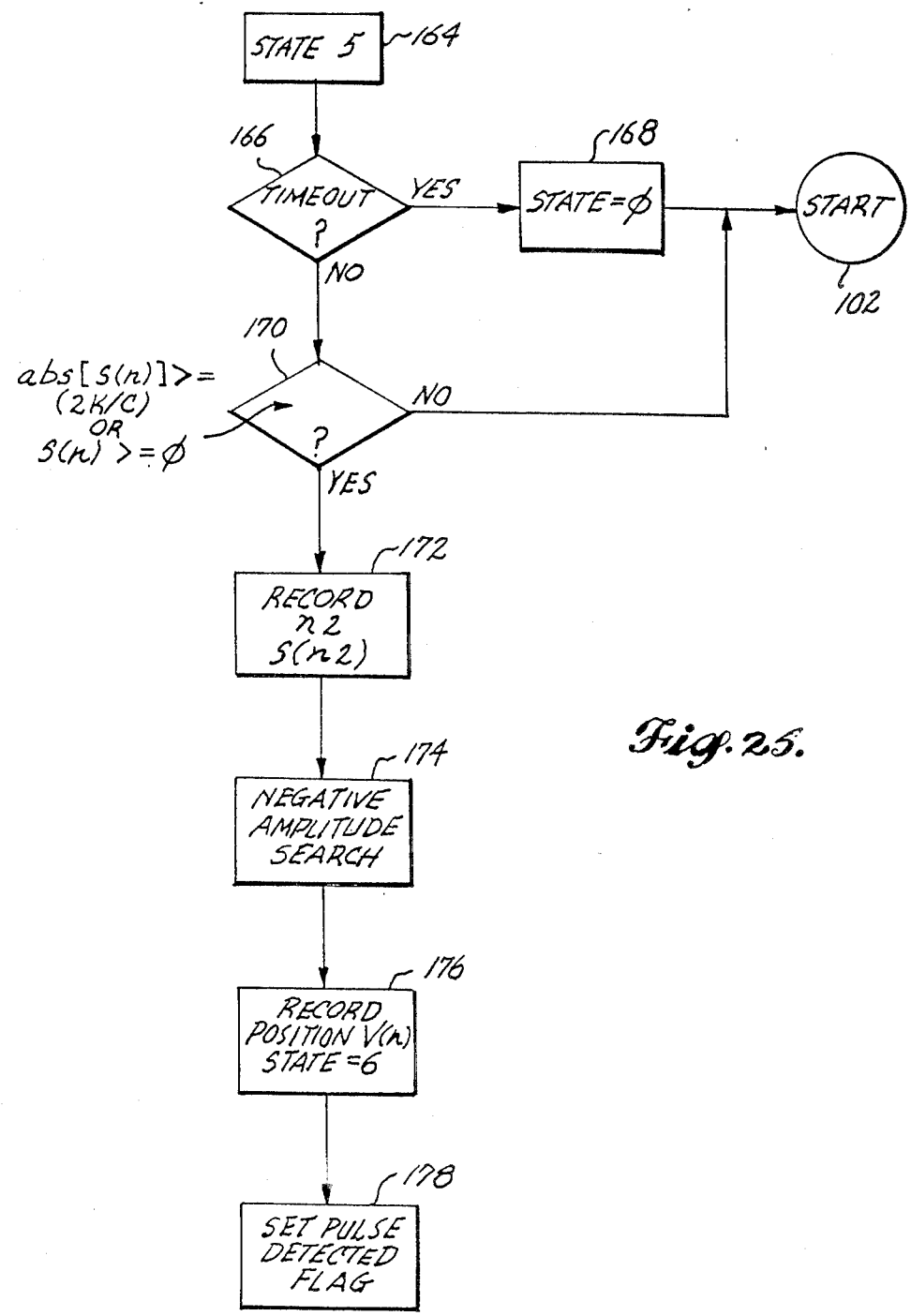

As shown in FIG. 25, the state six subroutine 178 sets a pulse detected flag indicating that a potential pulse, identified by positive and negative peaks, has been detected. This flag is then output to the waveform template comparator 88 for processing in the manner discussed below.

Before a more detailed description of the waveform template comparator block 88 is provided, however, a brief discussion of the template descriptors produced at block 90 for input to the comparator is provided. The template descriptors do not form a section of executable software but, rather, are a set of variables used to describe the features of the waveforms stored in data buffer 82. The group of descriptors collectively defines a template that can be compared against various parts of an incoming waveform to determine the existence and location of an arterial pulse admist, for example, artifact, noise, and dicrotic notches. As shown below, the descriptors employed are not constant. Rather, they are initialized with wide limits defining the most general shape of the pulse to be detected. They are then modified by the waveform template adaptor block 92 to better describe the particular waveform after a sufficient number of stable cycles of the waveform occur.

Figure 26:
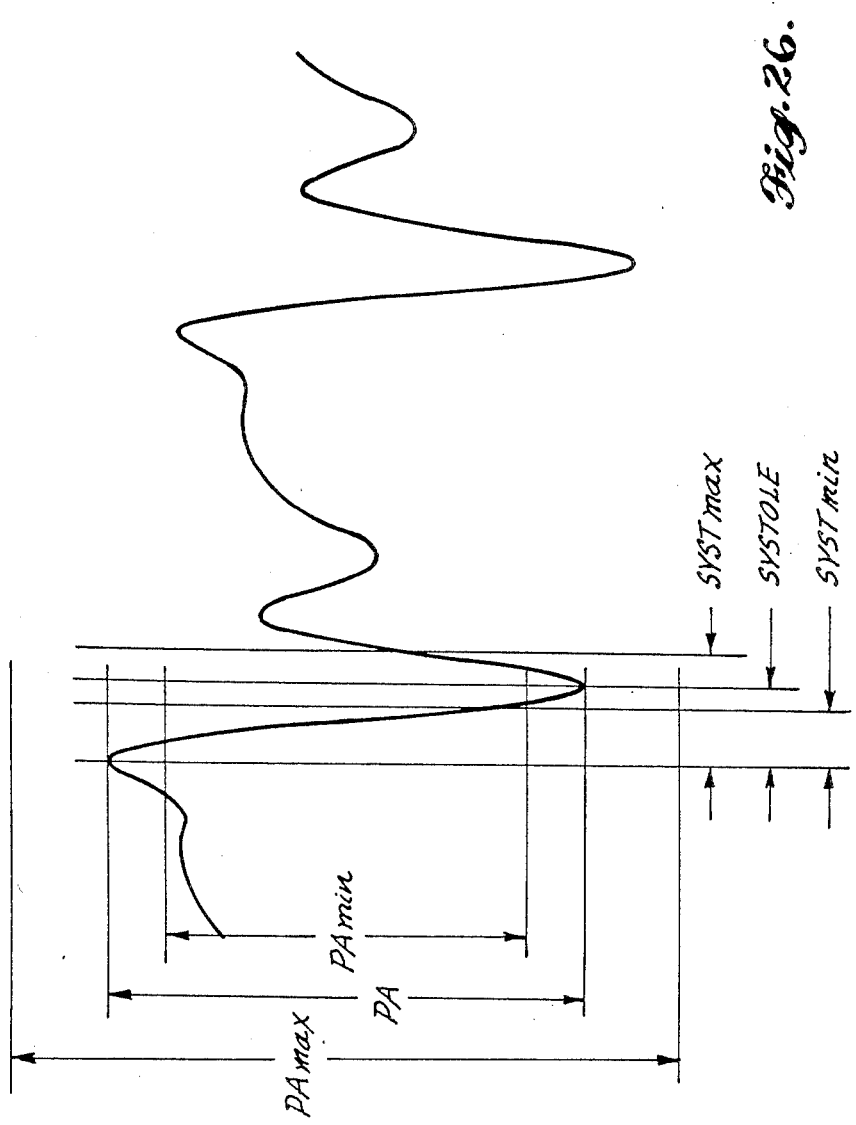
FIG. 26 is a graphical illustration of the waveform produced by the band-limiting block, showing the relationship of a plurality of waveform template descriptors to the waveform.

FIG. 26 is a plot of several periods of an exemplary waveform stored in data buffer 82. Shown in reference to a current systolic period, the descriptors include a maximum pulse amplitude ($PA_{max}$), minimum pulse amplitude ($PA_{min}$), maximum systole duration ($S_{max}$) and minimum systole duration ($S_{min}$). In addition to the features shown, the $\lambda$ pulse average amplitude ($PA_{avg}$) averaged over N pulses and a no-pulse counter are retained.

Figure 27:
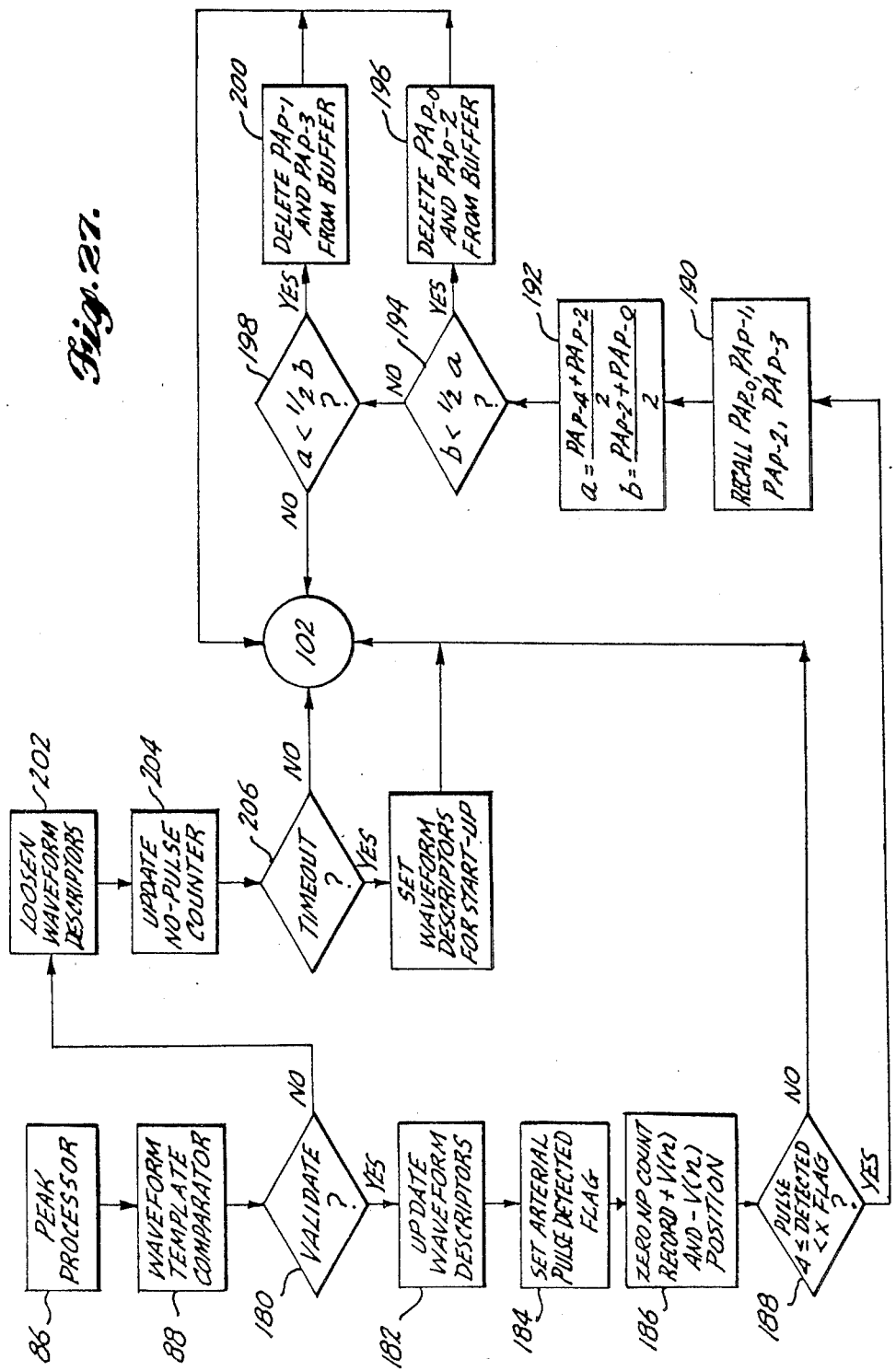
FIG. 27 is a more detailed block diagram of the waveform template comparator and waveform template adaptor blocks.

As shown in FIGS. 15 and 27, the flow of the program from the peak processor block 86 is to waveform template comparator 88. There, the pulses identified by the peak processor block 86 are compared against the template descriptors received from block 90. Basically, the comparator performs a validation test at block 180 that requires the pulse amplitude of the pulse identified by the peak processor 86 to be less than $PA_{max}$ and greater than $PA_{min}$. In addition, the systolic period of the pulse must be less than $S_{max}$ and greater than $S_{min}$. Values for the template descriptors used in the validation check at step 180 are initialized at start-up as follows. $PA_{max}$ is set to a predetermined constant factor CH0. $PA_{min}$ is set to a constant factor CL0. Similarly, $S_{max}$ is set to a constant factor PH0, while $S_{min}$ is set to PL0. Thus, the first time template comparator block 88 is accessed, these are the limits against which the pulse detected by peak processor block 86 is compared.

Assuming that a validated pulse is indicated by block 180, the waveform descriptor tolerances are updated at block 182. The validated pulse amplitude (being the difference between the positive and negative peaks detected) is added to a running average of the amplitudes of the last N−1 pulses detected. This updated pulse average is assigned to $PA_{avg}$ and is used in updating the amplitude limits in the following manner. With a validated pulse detected, the updating involves the tightening of the tolerances so that the descriptors converge on well behaved arterial pulses. In this case, $PA_{max}$ is reset to the product of $PA_{avg}$ and a constant limit factor CH1. Similarly, $PA_{min}$ is reset to the product of $PA_{avg}$ and a constant limit factor CL1.

The duration of systole for the newest arterial pulse detected is then used to update the systolic period limits in the following manner. $S_{max}$ is reset as the current arterial pulse systolic period plus the product of the current systolic period and a constant limit factor PH1. Similarly, $S_{min}$ is reset at the current arterial pulse systolic period minus the product of that period and a constant factor PL1. Because changes in systolic interval are relatively small in comparison to amplitude changes throughout the pulses detected, the relative changes in the amplitude descriptor limits are substantially grater than those of the systolic period descriptors.

With the waveform descriptor tolerances updated at block 182, the arterial pulse detected flag is set at block 184 before the positions in the data buffer 82 of the positive and negative voltages of the pulse detected are recorded at block 186. A no-pulse counter, described in greater detail below, is zeroed with the setting of the arterial pulse detected flag.

A test is performed at block 188 that produces a positive output only when the number of arterial pulses detected is greater than four but less than some predetermined number X. In that case, the waveform descriptor tolerances may not yet have been sufficiently adjusted to reject dicrotic notches from the pulses detected. Therefore, additional processing is implemented to eliminate the notches from the pulses retained in data buffer 82. As shown in FIG. 27, the pulse amplitude of the last detected pulse $PA_{P0}$ is recalled from data buffer 82 along with the pulse amplitude of the preceding three pulses detected $PA_{P-1}$, $PA_{P-2}$, and $PA_{P-3}$. Then, at block 192 a first average, a, of the pulse amplitudes $PA_{P-3}$ and $PA_{P-1}$ is produced. Likewise, a second average b of the pulse amplitudes $PA_{P-0}$ and $PA_P$ is produced. At step 194 a test is performed on these averages to determine whether b is less than one-half the value of a. It it is, the pulse amplitudes used to compute the average b are likely indicative of dicrotic notches and the pointers to these features are deleted from the buffer manager 100 at block 196.

If the outcome of the test performed at block 194 is false, however, a second test is performed at block 198 to determine whether a is less than one-half of b. If it is, the pulse amplitudes used to compute the average a are likely representative of dicrotic notches and the pointers to these features are deleted from the buffer manager 100 at step 200. Blocks 196 and 200 additionally decrement the arterial pulse counter by two. If the test at step 198 indicates that no dicrotic notches have been counted in the pulses detected, the program is returned to block 102. Likewise, if the initial test at block 188 had produced a negative output, the program would be returned via block 102.

Returning now to the validation test performed at block 180 by waveform template comparator 88, if the pulse detected by peak processor block 86 did not fall within the template descriptors produced via block 90, the descriptor tolerances are loosened at block 202. The loosening is accomplished in a manner similar to that of the tightening performed at block 182. More particularly, $PA_{max}$ is reset to $PA_{max}$ plus the product of PA$_{max}$ and a constant amplitude limit factor CH2. PA$_{min}$, on the other hand, is reset to PA$_{min}$ minus the product of PA$_{min}$ and a constant amplitude limit factor CL2. The adaptation of the systolic period descriptor limits is performed in the same manner as described for the tolerance adjustment at block 182. Because a validated pulse has not been detected in this loop through the software, a no-pulse counter is updated at block 204. A timeout test is performed at block 206 to determine whether a predetermined interval has been exceeded in the search for a valid pulse. If it has, the waveform descriptors are reinitiated to their start-up values discussed above at block 208 before the software is restarted via start block 102. Otherwise, the program progresses directly to block 102.

Figure 28:
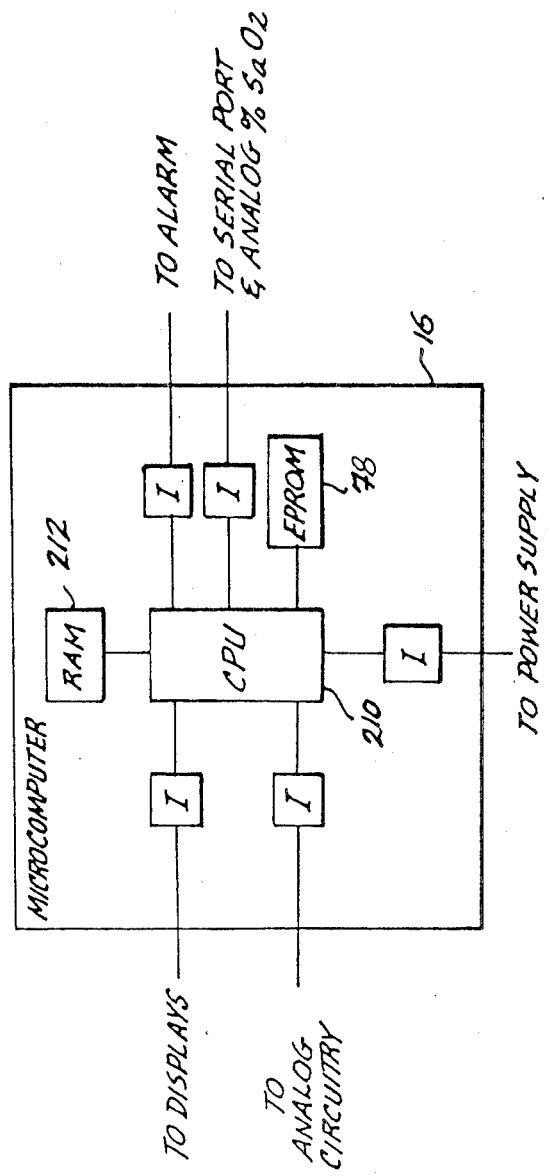
FIG. 28 is a more complete block diagram of the microcomputer illustrated in FIG. 1.

With values determined for R$_H$, R$_L$, IR$_H$, IR$_L$, and the signal period, the computational software in EPROM 78 causes CPU 210, shown in FIG. 28, to determine the present value for R$_{OS}$ by substituting the measured values for R$_H$, R$_L$, IR$_H$, and IR$_L$ into equation (22):

$$R_{OS} = \frac{\ln(R_L/R_H)}{\ln(IR_L/IR_H)} \quad (26)$$

Then, the computational software instructs CPU 210 to determine the oxygen saturation from R$_{OS}$ by use of a calibration curve, such as the one depicted in FIG. 7 and store that value in random-access memory 212. The calibration curve is a plot of the relationship between independently determined oxygen saturations corresponding to values of R$_{OS}$ produced by oximeter 10 in accordance with the technique described above.

With sufficiently large space in EPROM 78, enough points along the calibration curve can be stored in a look-up table to allow CPU 210 to extract an accurate indication of oxygen saturation from the value of R$_{OS}$ input to EPROM 78. The storage of a sufficient number of calibration curve data points may, however, necessitate the use of an undesirably large-capacity EPROM 78. For that reason, a second method of storing the calibration curve information may be preferred.

Pursuant to that method, once independently derived data associating R$_{OS}$ with the oxygen saturation are obtained, a mathematical expression between the two can be derived from a plot of the curve. The basic formula and the coefficients of the formula's variables are then stored in EPROM 78. When a value for R$_{OS}$ is measured, CPU 210 extracts the coefficients from EPROM 78 and computes a value for the oxygen saturation. This technique allows information completely identifying the entire calibration curve, or a family of such curves, to be stored within a relatively small amount of EPROM 78 space.

The computational software in EPROM 78 also instructs CPU 210 to determine the pulse rate from the signal period. Displays 20 then provide visible and audible outputs of the oxygen saturation and pulse rate in a manner conveniently used by the operator of oximeter 10.

While the references have been described with reference to a preferred embodiment, it is to be clearly understood by those skilled in the art that the invention is not limited thereto, and that the scope of the invention is to be interpreted only in conjunction with the following claims.

The embodiments of the invention in which an exclusive property or privilege is claimed are defined as follows:

1. An apparatus for processing a signal containing information about arterial blood flowing in tissue, said signal having a relatively periodic pulsatile component superimposed upon a varying baseline component, said apparatus comprising:

first portion identification means for identifying a first portion of said signal during which the sign of the slope of said signal changes from positive to negative;

positive peak location means for locating the point along said first portion of said signal having the largest amplitude, the point having said largest amplitude defining a positive peak of said signal;

second portion identification means for identifying a second portion of said signal during which the sign of the slope of said signal changes from negative to positive;

negative peak location means for locating the point along said second portion of said signal having the smallest amplitude, the point having said smallest amplitude defining a negative peak of said signal and the difference in signal amplitude between said positive peak and said negative peak defining a pulse amplitude; and analyzing means, responsive to said positive and negative peak location means, for producing an output indicative of a characteristic of said arterial blood.

2. The apparatus of claim 1, wherein said first portion identification means and said second portion identification means further comprise:

derivative computation means for producing an indication of the first derivative of said signal with respect to time;

first marker means for identifying an initial point on said signal at which the absolute value of said indication crosses below a predetermined threshold; and second marker means for identifying the point on said signal at which the absolute value of said indication first crosses back above said predetermined threshold.

3. The apparatus of claim 2, wherein said indication produced by said derivative computation means comprises an autonormalized convolution derivative of the signal determined in accordance with the relationship:

$$S(n) = \sum_{j=n-(k+1)}^{n+k} \text{sign}[V(j) - V(j-1)]$$

where:

n is the sample time for which the autonormalized convolution derivative is determined;

j is a summation index;

V(j) is the amplitude of said signal at a sample time j; and k is an integer used to define the range over which the samples are summed.

4. The apparatus of claim 3, wherein S(n) is determined for k equal to three.

5. The apparatus of claim 1, further comprising positive slope detection means for determining when said slope of said signal has been positive for some predetermined time, said first portion detection means being inhibited from identifying said first portion of said signal until said predetermined time has been exceeded.

6. The apparatus of claim 1, further comprising period determination means for determining the time interval occurring between said positive peak and said negative peak of said sample.

7. The apparatus of claim 1, wherein said first portion identification means, positive peak location means, second portion identification means and negative peak location means cooperatively produce a plurality of pairs of said positive and negative peaks.

8. The apparatus of claim 1, wherein said characteristic indicated by said output of said analyzing means includes pulse rate and oxygen saturation.

9. The apparatus of claim 1, further comprising rejection means for rejecting said positive and negative peaks when said peaks fail to satisfy a selection criterion.

10. The apparatus of claim 9, wherein said criterion comprises a pulse amplitude template defining an allowable pulse amplitude range, said rejection means rejecting said positive and negative peaks when said pulse amplitude is outside of said allowable pulse amplitude range.

11. The apparatus of claim 10, wherein said allowable pulse amplitude range is adjustable.

12. The apparatus of claim 11, wherein said allowable pulse amplitude range is initialized at a predetermined level.

13. The apparatus of claim 11, wherein said allowable pulse amplitude range is automatically increased in porportion to said pulse amplitude when said pulse amplitude is outside of said allowable range and decreased in portion to said pulse amplitude when said pulse amplitude is within said allowable range.

14. The apparatus of claim 10, wherein said criterion further comprises a systolic interval template, the time between said positive peak and said negative peak defining a systolic interval, said systolic interval template defining an allowable systolic interval range, said rejection means rejecting said positive and negative peaks when said systolic interval is outside of said allowable systolic interval range.

15. The apparatus of claim 9, wherein said criterion comprises a systolic interval template, the time between said positive peak and said negative peak defining a systolic interval, said systolic interval template defining an allowable systolic interval range, said rejection means rejecting said positive and negative peaks when said systolic interval is outside of said allowable systolic interval range.

16. The apparatus of claim 15, wherein said allowable systolic interval range is adjustable.

17. The apparatus of claim 16, wherein said allowable systolic interval range is initialized at a predetermined level.

18. The apparatus of claim 16, wherein said allowable systolic interval range is increased in proportion to said systolic interval when said systolic interval is outside of said allowable systolic interval range and decreased in proportion to said systolic interval when said systolic interval is within said allowable range.

19. The apparatus of claim 9, further comprising means for comparing an average of said pulse amplitudes determined at a first and third pulse with an average determined at a second and fourth pulse, said first, second, third and fourth pulses being consecutive pulses of said arterial blood flowing in said tissue.

20. The apparatus of claim 1, further comprising means for band-limiting said signals.

21. The apparatus of claim 1, further comprising a differential, current-to-voltage amplifier for amplifying said signals.

22. A method for processing a signal containing information about arterial blood flowing in tissue, said signal having a relatively periodic pulsatile component superimposed upon a varying baseline component, said method comprising the steps of:
   identifying a first portion of said signal during which the sign of the slope of said signal changes from positive to negative;
   locating the point along said first portion of said signal having the largest amplitude, the point having said largest amplitude defining a positive peak of said signal;
   identifying a second portion of said signal during which the sign of the slope of said signal changes from negative to positive;
   locating the point along said second portion of said signal having the smallest amplitude, the point having said smallest amplitude defining a negative peak of said signal and the difference in signal amplitude between said positive peak and said negative peak defining a pulse amplitude; and
   producing an output indicative of a characteristic of said arterial blood in response to said positive and negative peaks.

23. The method of claim 22, wherein said step of identifying said first and second portions of said signal further comprises the steps of:
   producing an indication of the first derivative of said signal with respect to time;
   identifying an initial point on said signal at which the absolute value of said indication crosses below a predetermined threshold; and
   identifying the point on said signal at which the absolute value of said indication first crosses back above said predetermined threshold.

24. The method of claim 23, wherein said step of producing an indication of the first derivative of said signal with respect to time comprises producing an autonormalized convolution derivative of the signal determined in accordance with the relationship:

$$S(n) = \sum_{j=n-(k+1)}^{n+k} \text{sign}[V(j) - V(j-1)]$$

where:
   n is the sample time for which the autonormalized convolution derivative is determined;
   j is a summation index;
   V(j) is the amplitude of said signal at a sample time j; and
   k is an integer used to define the range over which the samples are summed.

25. The method of claim 24, wherein S(n) is determined for k equal to three.

26. The method of claim 22, further comprising the step of determining when said slope of said signal has been positive for some predetermined time before said step of identifying said first portion of said signal is performed.

27. The method of claim 22, further comprising the step of determining the time interval occurring between said positive peak and said negative peak of said sample.

28. The method of claim 22, wherein said steps of identifying said first portion of said signal, locating the point along said first portion of said signal having the largest amplitude, identifying said second portion of said signal, and locating the point along said second portion of said signal having the smallest amplitude cooperatively produce a plurality of pairs of said positive and negative peaks.

29. The method of claim 22, wherein said characteristic of said arterial blood flow indicated by said output includes pulse rate and oxygen saturation.

30. The method of claim 22, further comprising the step of rejecting the positive and negative peaks when said peaks fail to satisfy a selection criterion.

31. The method of claim 30, wherein said criterion comprises a pulse amplitude template defining an allowable pulse amplitude range, said positive and negative peaks being rejected when said pulse amplitude is outside of said allowable pulse amplitude range.

32. The method of claim 31, wherein said allowable pulse amplitude range is adjustable.

33. The method of claim 32, wherein said allowable pulse amplitude range is initialized at a predetermined level.

34. The method of claim 32, wherein said allowable pulse amplitude range is automatically increased in proportion to said pulse amplitude when said pulse amplitude is outside of said allowable range and decreased in proportion to said pulse amplitude when said pulse amplitude is within said allowable range.

35. The method of claim 31, wherein said criterion further comprises a systolic interval template, the time between said positive peak and said negative peak defining a systolic interval, said systolic interval template defining an allowable systolic interval range, said positive and negative peaks being rejected when said systolic interval is outside of said allowable systolic interval range.

36. The method of claim 30, wherein said criterion comprises a systolic interval template, the time between said positive peak and said negative peak defining a systolic interval, said systolic interval template defining an allowable systolic interval range, said positive and negative peaks being rejected when said systolic interval is outside of said allowable systolic interval range.

37. The method of claim 36, wherein said allowable systolic interval range is adjustable.

38. The method of claim 37, wherein said allowable systolic interval range is initialized at a predetermined level.

39. The method of claim 37, wherein said allowable systolic interval range is increased in proportion to said systolic interval when said systolic interval is outside of said allowable systolic interval range and decreased in proportion to said systolic interval when said systolic interval is within said allowable range.

40. The method of claim 30, further comprising the step of comparing an average of said pulse amplitudes determined at a first and third pulse with an average determined at a second and fourth pulse, said first, second, third and fourth pulses being consecutive pulses of said arterial blood flowing in said tissue.

41. The method of claim 22, further comprising the step of band-limiting said signals.

42. An apparatus for processing a signal containing information about arterial blood, said signal having a relatively periodic pulsatile component superimosed upon a variable baseline component, said apparatus comprising:
positive peak identification means for employing an autonormalized convolution derivative of said signal to identify a positive peak of said signal;
negative peak identification means for employing an autonormalized convolution derivative of said signal to identify a negative peak of said signal; and
analyzing means, responsive to said positive and negative peak idenfication means, for producing an output indicative of a characteristic of said arterial blood.

43. A method of processing a signal containing information about arterial blood, said signal having a relatively periodic pulsatile component superimposed upon a variable baseline component, said method comprising the steps of:
determining the autonormalized convolution derivative of said signal;
employing said autonormalized convolution derivative to identify a positive peak of said signal and a negative peak of said signal; and
producing an output indicative of a characteristic of said arterial blood in response to said positive and negative peaks.

* * * * *

UNITED STATES PATENT AND TRADEMARK OFFICE
CERTIFICATE OF CORRECTION

PATENT NO. : 4,800,495

DATED : January 24, 1989

INVENTOR(S) : Robert E. Smith

It is certified that error appears in the above-identified patent and that said Letters Patent is hereby corrected as shown below:

| Column | Line | |
|---|---|---|
| 3  | 30 | "disclose" should be --discloses-- |
| 3  | 37 | insert --and-- after "red" |
| 9  | 20 | delete "ti" before equation (3) |
| 11 | 31 | "distole" should be --diastole-- |
| 11 | 59 | "$L_{0e}$" should be --$I_0 e$--; "$\alpha_A \alpha d$" should be --$\alpha_A \Delta d$-- |
| 12 | 3  | "-$\Delta d$" should be ---$\alpha d$-- (in the denominator) |
| 15 | 19 | "mesurement" should be --measurement-- |
| 15 | 60 | insert --is-- before "also" |
| 18 | 60 | "are" should be --and-- (second occurrence) |
| 19 | 60 | "idicated" should be --indicated-- |
| 21 | 65 | "samples" should be --sample-- |
| 22 | 47 | "to" should be --and-- |
| 23 | 26 | "admist" should be --amidst-- |
| 24 | 18 | "grater" should be --greater-- |
| 24 | 41 | "$PA_{p-0}$" should be --$PA_{p-2}$--; "$PA_p$" should be --$PA_{p-0}$-- |
| 27 | 33 | "portion" should be --proportion-- |
| 30 | 32 | "idenfication" should be --identification-- |

Signed and Sealed this

Twenty-first Day of April, 1992

Attest:

HARRY F. MANBECK, JR.

*Attesting Officer*        *Commissioner of Patents and Trademarks*